United States Patent
Ni et al.

(10) Patent No.: US 7,252,640 B2
(45) Date of Patent: Aug. 7, 2007

(54) DETECTION OF DISORDERED BREATHING

(75) Inventors: Quan Ni, Saint Paul, MN (US); John D. Hatlestad, Maplewood, MN (US); Jesse W. Hartley, Lino Lakes, MN (US); Jeff E. Stahmann, Ramsey, MN (US); Jaeho Kim, Redmond, WA (US); Kent Lee, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 585 days.

(21) Appl. No.: 10/309,770

(22) Filed: Dec. 4, 2002

(65) Prior Publication Data

US 2004/0111040 A1 Jun. 10, 2004

(51) Int. Cl.
*A61B 5/02* (2006.01)
(52) U.S. Cl. .................... 600/538; 600/532
(58) Field of Classification Search ............. None
See application file for complete search history.

(56) References Cited

U.S. PATENT DOCUMENTS

| | | | |
|---|---|---|---|
| 4,827,935 A | 5/1989 | Geddes et al. | |
| 5,146,918 A | 9/1992 | Kallok et al. | |
| 5,178,156 A | 1/1993 | Takishima et al. | |
| 5,233,983 A | 8/1993 | Markowitz | |
| 5,335,657 A | 8/1994 | Terry, Jr. et al. | |
| 5,944,680 A | 8/1999 | Christopherson et al. | |
| 6,064,910 A | 5/2000 | Andersson et al. | |
| 6,120,441 A | 9/2000 | Griebel | |
| 6,126,611 A | 10/2000 | Bourgeois et al. | |
| 6,132,384 A | 10/2000 | Christopherson et al. | |
| 6,589,188 B1 * | 7/2003 | Street et al. ............. | 600/538 |
| 6,752,765 B1 * | 6/2004 | Strobel et al. ............ | 600/536 |
| 6,752,766 B2 * | 6/2004 | Kowallik et al. ........... | 600/538 |
| 6,810,287 B2 * | 10/2004 | Zhu et al. ................ | 607/17 |
| 6,881,192 B1 * | 4/2005 | Park ...................... | 600/529 |

FOREIGN PATENT DOCUMENTS

| | | |
|---|---|---|
| EP | 1 151 718 A | 7/2001 |
| EP | 1 317 943 A | 11/2003 |
| WO | WO 00/01438 A | 1/2000 |

* cited by examiner

Primary Examiner—Robert L. Nasser
(74) Attorney, Agent, or Firm—Hollingsworth & Funk, LLC

(57) ABSTRACT

Devices and methods for detecting disordered breathing involve determining that the patient is asleep and sensing one or more signals associated with disordered breathing indicative of sleep-disordered breathing while the patient is asleep. Sleep-disordered breathing is detected using the sensed signals associated with disordered breathing. The sensed signals associated with disordered breathing may also be used to acquire a respiration pattern of one or more respiration cycles. Characteristics of the respiration pattern are determined. The respiration pattern is classified as a disordered breathing episode based on the characteristics of the respiration pattern. One or more processes involved in the detection of disordered breathing are performed using an implantable device.

44 Claims, 20 Drawing Sheets

DETECTION OF DISORDERED BREATHING

FIELD OF THE INVENTION

The present invention relates generally to detecting disordered breathing, including sleep and non-sleep disordered breathing.

BACKGROUND OF THE INVENTION

Sleep is generally beneficial and restorative to a patient, exerting great influence on the quality of life. A typical night's sleep for a normal person begins with a sleep stage known as slow wave sleep (SWS) characterized by low frequency electroencephalogram (EEG) activity. As the person falls asleep, brain activity declines and there is a progressive increase in the depth of sleep. At approximately ninety minute intervals, sleep lightens and a sleep stage known as rapid eye movement (REM) sleep is initiated. REM sleep is characterized by high frequency EEG activity, bursts of rapid eye movements, skeletal muscle atonia, and heightened autonomic activity.

There are typically 4-6 REM periods per night, with increasing duration and intensity toward morning. While dreams can occur during either REM or SWS sleep, the nature of the dreams varies depending on the type of sleep. REM sleep dreams tend to be more vivid and emotionally intense than SWS sleep dreams. Furthermore, autonomic nervous system activity is dramatically altered when REM sleep is initiated.

In patients with respiratory or heart disease, the brain during sleep can precipitate breathing disturbances, myocardial ischemia, or arrhythmia. Although REM sleep is a necessary component of normal sleep, serious consequences may be associated with both the increase in autonomic activity and the intense emotional responses that accompany dreaming in patients with cardiovascular disease or respiratory disorders, for example.

Disruptions of the respiratory system during sleep may include the conditions of sleep apnea or sleep hypopnea. Sleep apnea is a serious breathing disorder caused by airway obstruction, denoted obstructive sleep apnea, or derangement in central nervous system control of respiration, denoted central sleep apnea. Regardless of the type of apnea, people with sleep apnea stop breathing repeatedly during their sleep, sometimes hundreds of times a night and often for a minute or longer. Whereas sleep apnea refers to cessation of breathing, hypopnea is associated with periods of abnormally slow or shallow breathing. With each apnea or hypopnea event, the person generally briefly arouses to resume normal breathing. As a result, people with sleep apnea or hypopnea may experience sleep fragmented by frequent arousals.

An adequate quality and quantity of sleep is required to maintain physiological homeostasis. Prolonged sleep deprivation or periods of highly fragmented sleep ultimately will have serious health consequences. Chronic lack of sleep may be associated with various cardiac or respiratory disorders affecting a patient's health and quality of life.

SUMMARY OF THE INVENTION

Various embodiments of the present invention involve detecting disordered breathing including sleep apnea and hypopnea. In one embodiment of the invention, a method for detecting disordered breathing involves determining that the patient is sleeping and sensing one or more signals indicative of disordered breathing while the patient is asleep. Disordered breathing is detected using the one or more sensed signals. At least one of determining the patient is asleep, sensing signals while the patient is asleep, and detecting disordered breathing is performed at least in part implantably.

In another embodiment of the invention, a method for detecting sleep-disordered breathing involves detecting respiration patterns of one or more respiration cycles. One or more characteristics of the respiration patterns are determined. The respiration patterns are classified as disordered breathing based on the characteristics of the respiration patterns.

Another embodiment of the invention includes a device for detecting sleep disordered breathing comprising a sensor system configured to sense one or more signals indicative of disordered breathing. The device also includes a sleep detector configured to determine that a patient is asleep. The device further includes a disordered breathing detector coupled to the sensor system and the sleep detector. The disordered breathing detector is arranged to detect disordered breathing based on an output of the sleep detector and the one or more signals indicative of sleep disordered breathing. At least one of the sensor system, the sleep detector, and the disordered breathing detector uses an implantable device.

A further embodiment of the invention includes a sleep-disordered breathing detection device comprising a sensor system configured to detect a respiration pattern of one or more respiration cycles. The device further includes a detector system coupled to the sensor system. The detector system is configured to determine one or more characteristics of the respiration pattern and classify the respiration pattern as disordered breathing using the one or more characteristics of the respiration pattern. At least one of the sensor system and the detector system uses an implantable device.

Another embodiment of the invention involves a system for detecting disordered breathing including means for determining that the patient is asleep, means for sensing, while the patient is asleep, one or more signals indicative of disordered breathing, and means for detecting disordered breathing based on the one or more sensed signals, wherein at least one of the means for determining, means for sensing, and means for detecting uses an implantable device.

In yet another embodiment of the invention, a sleep-disordered breathing detection system includes means for detecting a respiration pattern of one or more respiration cycles, means for determining one or more characteristics of the respiration pattern, and means for classifying the respiration pattern as sleep-disordered breathing based on the one or more characteristics of the respiration pattern, wherein at least one of the means for detecting, means for determining, and means for classifying uses an implantable device.

Another method for detecting disordered breathing in a patient in accordance with an embodiment of the invention includes detecting a respiration pattern of one or more respiration cycles. Characteristics of the respiration pattern are determined and the respiration pattern is classified as disordered breathing based on the characteristics. At least one of detecting, determining and classifying is performed at least in part implantably.

Another embodiment of the invention includes a disordered breathing detection device comprising a sensor system configured to detect a respiration pattern of one or more respiration cycles. The device further includes a detector system coupled to the sensor system. The detector system is configured to determine one or more characteristics of the respiration pattern and classify the respiration pattern as disordered breathing using the one or more characteristics of the respiration pattern. At least one of the sensor system and the detector system uses an implantable component.

In a further embodiment of the invention, a disordered breathing detection system includes means for detecting a respiration pattern of one or more respiration cycles, means for determining one or more characteristics of the respiration pattern, and means for classifying the respiration pattern as disordered breathing based on the one or more characteristics of the respiration pattern, wherein at least one of the means for detecting, means for determining, and means for classifying uses an implantable component.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
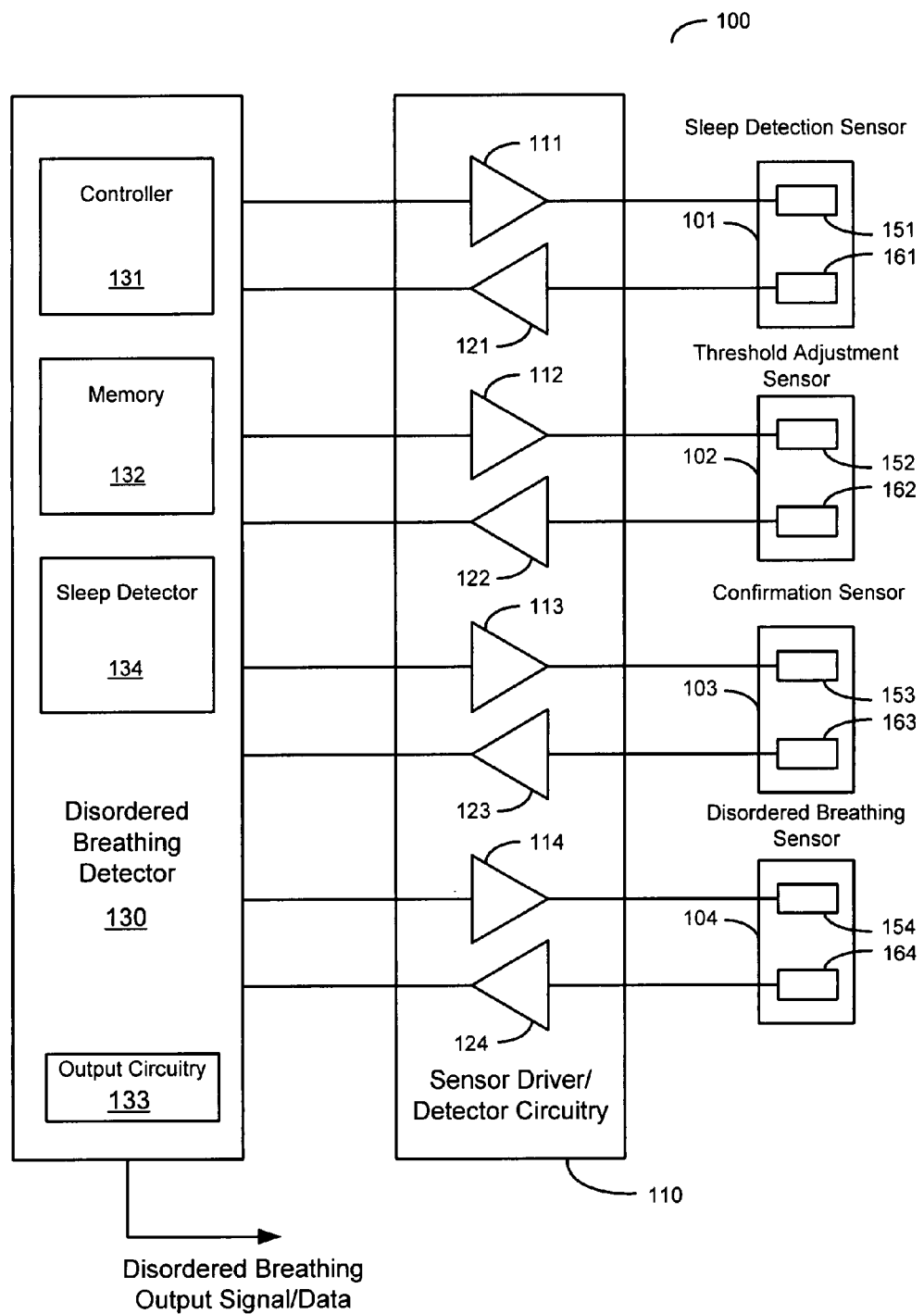
FIG. 1 is a block diagram of a disordered breathing detector in accordance with an embodiment of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

An adequate duration and quality of sleep is required to maintain physiological homeostasis. Prolonged sleep deprivation or periods of poor quality sleep ultimately will have serious health consequences. Disordered breathing, such as sleep apnea and hypopnea, is a major cause of interrupted sleep. People suffering from sleep apnea repeatedly stop breathing during sleep. Hypopnea is a related condition, characterized by periods of abnormally slow or shallow breathing.

Sleep apnea/hypopnea may be obstructive, central, or a mixture of the two types. Obstructive sleep apnea/hypopnea is the most common type and is typically caused by a blockage of the airway, usually when the soft tissue in the throat collapses and closes during sleep. In central sleep apnea/hypopnea, the airway is not blocked but there is an interruption in signals from the brain controlling breathing. With each apnea/hypopnea event, the person may briefly arouse in order to resume breathing. The frequent interruptions during sleep result in extremely fragmented sleep of poor quality. Untreated, sleep apnea/hypopnea has a number of adverse health and quality of life consequences ranging from high blood pressure and other cardiovascular diseases to memory problems, headaches and degradation of social and work related activities.

Diagnosis of the conditions causing sleep disturbances, including disordered breathing, may require people suffering from sleep disorders to spend one or more nights in a sleep laboratory. In the sleep laboratory setting, a patient can be instrumented for data acquisition and observed by trained personnel. Polysomnography may be used to diagnose and determine the severity of sleep apnea/hypopnea. During this procedure, a variety of physiological functions are externally detected and recorded during sleep, such as the electrical activity in the brain, eye movement, muscle activity, heart rate, respiratory effort, and blood oxygen levels. Manual evaluation of these physiological functions is performed by a technician and used to diagnose disordered breathing such as sleep apnea/hypopnea and assess possible therapeutic interventions.

Testing in a sleep laboratory setting presents a number of obstacles in acquiring an accurate picture of a patient's typical sleep patterns. For example, spending a night in a laboratory typically causes a patient to experience a condition known as "first night syndrome," involving disrupted sleep during the first few nights in an unfamiliar location. Furthermore, sleeping while instrumented and observed may not result in a realistic perspective of the patient's normal sleep patterns.

Accurate detection of the type, onset, termination, frequency, duration, and severity of disordered breathing may be helpful in tailoring appropriate therapy for patients suffering from sleep disorders. Sleep apnea/hypopnea may be treated in a number of ways, including electrical stimulation therapy including cardiac rhythm management therapy (CRM) and/or hypoglossal nerve stimulation, for example. Respiratory therapy for sleep apnea/hypopnea may include techniques such as continuous positive airway pressure (CPAP). Mechanical therapy, ranging from dental appliances that reposition the lower jaw to surgical techniques such as uvulopalatopharyngoplasty (UPPP), a procedure to remove excess tissue at the back of the throat, may also be used. Each of these methods, as well as other methods for treating breathing disorders, may be improved by reliable detection of the type and severity of sleep apnea or hypopnea.

Various embodiments of the invention involve detecting disordered breathing based on one or more sensed signals. One embodiment of the invention involves determining that the patient is asleep, sensing signals indicative of disordered breathing, and detecting disordered breathing based on the sensed signals. Methods of sleep detection are described in commonly owned U.S. Pat. No. 7,189,204, which is hereby incorporated by reference.

According to certain embodiments of the invention, at least one of the steps of determining sleep, sensing the signals associated with disordered breathing, and detecting disordered breathing is implemented using an implantable device. For example, the signals associated with disordered breathing may be sensed using implantable sensors and analyzed by an external disordered breathing detector. In one configuration, some or all of the sensors may have remote communication capabilities, such as a wireless Bluetooth communications link. The wireless communications link couples the internal sensor or sensors to the external disordered breathing detector. The sensed signals are transmitted from the internal sensors to the external disordered breathing detector over the wireless communications link.

In another example, the disordered breathing detector is an implantable device and one or all of the sensors are located externally on or near the patient. The sensed signals are transmitted from the external sensors to the implanted disordered breathing detector over a wireless communication link.

Another embodiment of the invention involves detection of a respiration pattern of one or more respiration cycles and determining the characteristics of the respiration pattern. A respiration pattern is classified as disordered breathing based on the characteristics of the respiration patterns. At least one of detecting the respiration pattern, determining the characteristics of the respiration pattern, and classifying the respiration patterns is performed at least in part implantably.

In one configuration, the disordered breathing detector is a component of a device that also performs other functions, such as cardiac pacemaker or defibrillation functions. One or all of the sensors may be wirelessly coupled to the implantable device, for example. Respiration patterns may be classified by determining inspiration, expiration, and non-breathing intervals. Characteristics of the respiration patterns include respiration rate, respiration tidal volume, and duration of respiration cycle intervals and/or duration of the respiration pattern. Each characteristic of a respiration pattern may be expressed as a median, moving average, or weighted average, for example.

Indices associated with disordered breathing conditions are established. The indices may represent values or characteristics of the sensed signals associated with disordered breathing that indicate disordered breathing is occurring. The indices may be established using clinical data acquired from a similarly situated group of patients, or from the patient for whom disordered breathing is to be detected. Furthermore, the apnea or hypopnea indices established for a particular patient may take into account the presence of patient conditions such as cardiopulmonary diseases, e.g., heart failure and/or chronic obstructive pulmonary disease.

Disordered breathing may be detected by comparing one or more disordered breathing indices to the sensed signals associated with disordered breathing. In one example, disordered breathing is determined by comparing disordered breathing indices to characteristics of respiration patterns classified in accordance with the principles of the invention.

Another embodiment of the invention involves detecting disordered breathing episodes based on one or more breaths of excessive duration or insufficient volume. According to this embodiment, an apnea episode is detected if a breath interval exceeds a duration threshold. A hypopnea episode is detected if the tidal volume of successive breaths remains less than the tidal volume threshold for a period in excess of the duration threshold. Mixed apnea/hypopnea episodes may also occur, wherein the period of disordered breathing is characterized by shallow breaths and non-breathing intervals. During the mixed apnea/hypopnea episodes, the tidal volume of each breath remains less than the tidal volume threshold and one or more breath intervals exceeds a period exceeding the duration threshold.

According to an embodiment of the present invention, methods of disordered breathing detection are implemented in an implantable cardiac rhythm management (CRM) system configured as a dual chamber pacemaker device that may operate in numerous pacing modes known in the art. Systems and methods of the present invention may also be implemented in various types of implantable or external diagnostic medical devices including, for example, polysomnography devices, respiratory monitors, and cardiac monitors. In addition, methods of the present invention may be implemented in a number of implantable or external therapeutic medical devices such as continuous positive airway pressure (CPAP) devices or hypoglossal nerve stimulators.

FIG. 1 is a block diagram of a disordered breathing detection device 100 that may be used to detect disordered breathing in accordance with various embodiments of the invention. The disordered breathing detection device 100 includes a number of sensors 101, 102, 103, 104 that sense signals associated with sleep and/or disordered breathing. These signals may be processed to produce signal parameters associated with sleep and/or disordered breathing. For example, an electrical cardiac signal may be sensed and cardiac signal parameters including heart rate and QT interval may be determined from the electrical cardiac signal. In the context of the present invention, either a sensed signal or a derived signal parameter is generally referred to herein with the term signal.

A representative set of signals associated with sleep and/or disordered breathing include body movement, heart rate, QT interval, eye movement, respiration rate, transthoracic impedance, tidal volume, minute ventilation, body posture, electroencephalogram (EEG), electrocardiogram (ECG), electrooculogram (EOG), electromyogram (EMG), muscle tone, body temperature, pulse oximetry, blood pressure, time of day, and historical sleep times.

According to various embodiments, a set of sleep-related signals may be used for sleep detection and a separate or overlapping set of signals associated with disordered breathing may be used for disordered breathing detection. Sleep detection involves comparing a sleep detection signal derived from a sleep detection sensor 101 to a sleep threshold or index to detect the onset and termination of sleep. The sleep threshold may be a particular value of the sleep detection signal or another feature of the signal. A second sleep-related signal derived from a threshold adjustment sensor 102 may be used to adjust the sleep threshold or index. Although one sleep detection sensor and one threshold adjustment sensor are shown in FIG. 1, any number of sleep thresholds corresponding to any number of sleep detection sensors may be used. Furthermore, signals from any number of threshold adjustment sensors may be used to adjust the values or features of the sleep thresholds associated with a plurality of sleep detection signals. Additional sleep-related signals derived from one or more sleep confirmation sensors 103 may be used to confirm the onset and/or termination of the sleep condition.

In addition to the sleep detection sensors discussed above, one or more disordered breathing sensors 104 may be used to detect episodes of disordered breathing such as sleep apnea or hypopnea, for example. In some cases, the signals derived from the sleep detection 101, threshold adjustment 102, and/or confirmation sensors 103 may also be used for disordered breathing detection. In other cases, one or more disordered breathing sensors 104 may sense a different set of signals than the sleep-related signals.

The outputs of sensors 101, 102, 103, 104 are received by a sensor driver/detector system 110 having detection circuitry 121, 122, 123, 124, that may include, for example, amplifiers, signal processing circuitry, timing, and/or A/D conversion circuitry for each sensor output. The driver/detector system 110 may further include sensor drive circuitry 111, 112, 113, 114 as required to activate the sensors 101, 102, 103, 104.

A disordered breathing detector 130, according to one embodiment, transmits control signals to the drive circuitry 111, 112, 113, 114 and receives signals from the detection circuitry 121, 122, 123, 124. The disordered breathing detector 130 may include a sleep detector 134 for determining the onset and termination of a sleep state. The disordered breathing detector 130 may also include a microprocessor controller 131 that cooperates with the sleep detector 134 and the memory circuitry 132 for implementing disordered breathing detection methods of the present invention. The memory circuitry 132 may be used to store program code and/or data to implement disordered breathing detection and to store thresholds or indices associated with sleep detection and disordered breathing detection, such as, sleep thresholds, and sleep apnea or hypopnea detection indices. The memory circuitry 132 may also be used to store historical data regarding disordered breathing episodes.

In one embodiment of disordered breathing detection, a sleep detector 134 is used to determine that the patient is asleep. The sleep detector 134 may be configured to compare the value of a first sleep-related signal, derived from a sleep detection sensor 101, to a sleep threshold adjusted by a second sleep-related signal, derived from a threshold adjustment sensor 102. Onset or termination of sleep may be determined in the sleep detector 134 based on the comparison of the value of the first sleep-related signal to the sleep threshold. The sleep detector 134 may use one or more sleep thresholds associated with one or more sleep-related signals derived from a number of sensors. Further, the sleep detector 134 may use one or more sleep-related signals to adjust the sleep thresholds. In addition, the sleep detector 134 may confirm the onset or termination of sleep using an additional number of sleep-related signals.

According to various embodiments, the disordered breathing detector 130 includes one or more sensors for sensing signals associated with disturbed breathing. The signals associated with disordered breathing may include signals associated with cardiac activity, such as electrical activity of the heart, and/or signals associated with respiration, including transthoracic impedance. The signals associated with cardiac activity may be used to derive parameters such as heart rate and QT interval. The signals associated with respiration, e.g., transthoracic impedance, may be used to derive parameters including respiration rate, tidal volume, and minute ventilation.

One method of disordered breathing detection involves sensing one or more respiration signals to detect a respiration pattern. For example, transthoracic impedance may be sensed and used to acquire patterns of respiration. Disordered breathing, such as sleep apnea and hypopnea, may be detected based on characteristics of the respiration patterns, including characteristics such as tidal volume, respiration rate, duration of the respiration pattern, and duration of one or more respiration intervals within the respiration pattern.

The disordered breathing detector 130 may include output circuitry 133 for communicating output signals associated with the detection and analysis of disordered breathing to other diagnostic or therapeutic devices, other components of the disordered breathing detection device, a data storage device or a display device. The output signals may include, for example, a sleep apnea or hypopnea detection signal indicating that sleep apnea/hypopnea has been detected, as well as data related to the disturbed breathing episodes, including data providing the severity and duration of one or more disordered breathing episodes. The disordered breathing detector may communicate with another device over a wired or wireless communication channel, for example.

The sensors 101, 102, 103, 104 may comprise implantable sensors and/or external sensors. In one embodiment, the sensors 101, 102, 103, 104 are coupled to the driver/detector circuitry 110 and thus to the detector 130 through a wired connection. In another embodiment, one or more of the sensors 101, 102, 103, 104 and the associated driver/detector circuitry 110 are incorporated into sensing devices that include wireless communication capabilities, e.g., a Bluetooth transmitter or transceiver, and may be coupled to the detector 130 through a wireless link. The detector 130 and driver/detector circuitry 110 may be incorporated into an implantable or external device.

Figure 2:
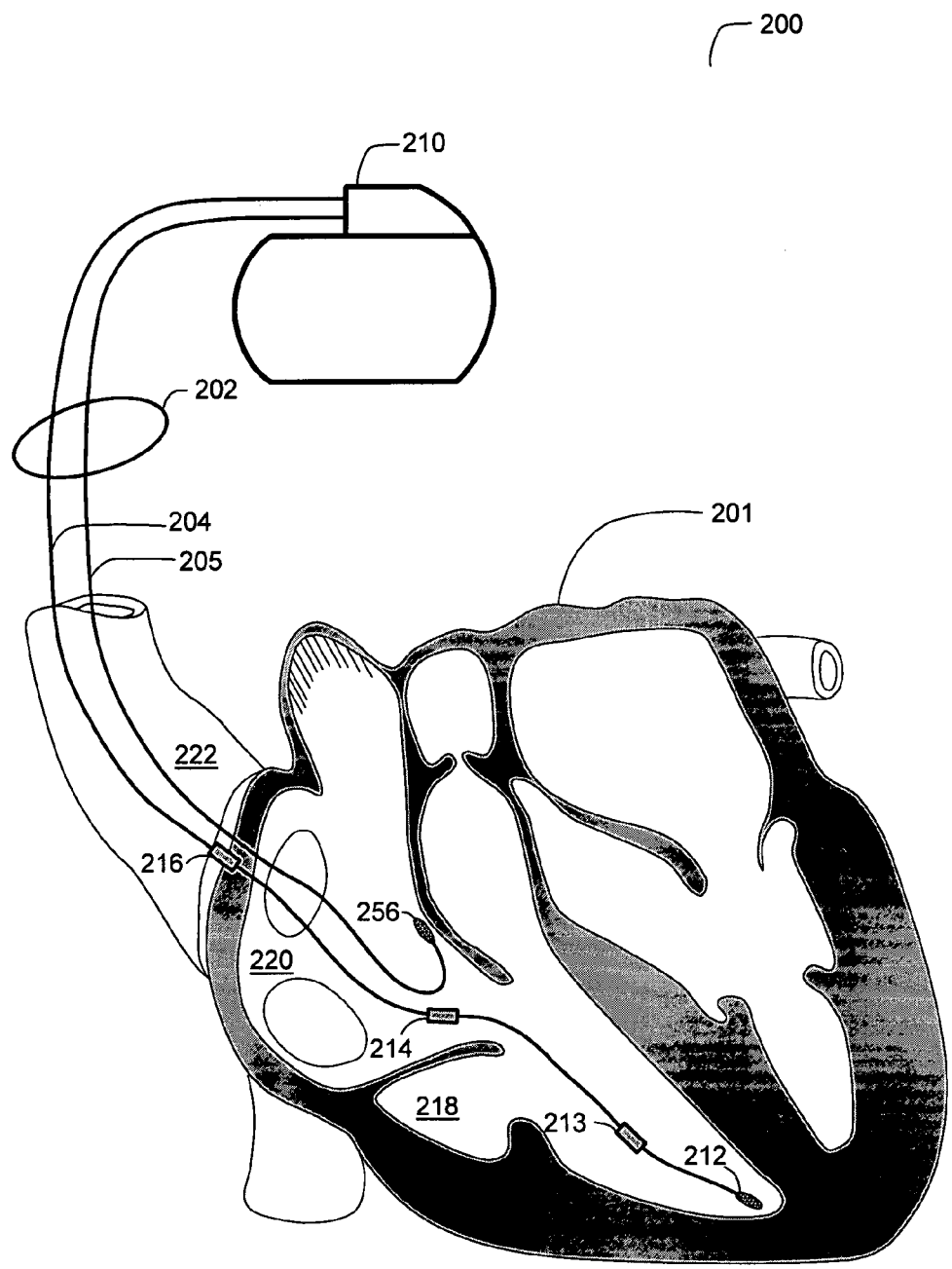
FIG. 2 is a partial view of one embodiment of an implantable medical device that may be used for detection of disordered breathing in accordance with an embodiment of the invention.

FIG. 2 is a partial view of one embodiment of an implantable medical device that may be used in connection with disordered breathing detection in accordance with the principles of the invention. The implantable device illustrated in FIG. 2 is a cardiac rhythm management (CRM)

system that includes an implantable pacemaker 200 electrically and physically coupled to an intracardiac lead system 202. The intracardiac lead system 202 is implanted in a human body with portions of the intracardiac lead system 202 inserted into a heart 201. The intracardiac lead system 202 is used to detect and analyze electric signals produced by the heart 201 and to provide electrical energy to the heart 201 under predetermined conditions to treat cardiac arrhythmias of the heart 201.

The CRM 200 depicted in FIG. 2 is a dual chamber device, capable of sensing signals from the right atrium and right ventricle and providing pacing pulses to the right atrium and the right ventricle. Low energy pacing pulses may be delivered to the heart to regulate the heart beat or maintain a lower rate heart beat, for example. In a configuration that includes cardioversion/defibrillation capabilities, high energy pulses may also be delivered to the heart if an arrhythmia is detected that requires cardioversion or defibrillation.

The intracardiac lead system 202 includes a right ventricular lead system 204 and a right atrial lead system 205. The right ventricular lead system 204 includes an RV-tip pace/sense electrode 212 and one or more impedance electrodes 213, 214, 216 suitable for measuring transthoracic impedance. In one configuration, impedance sense and drive electrodes 216, 214, 213 may be configured as ring electrodes.

The right ventricular lead system 204 depicted in FIG. 2 includes an impedance drive electrode 213 located in the right ventricle 218. The right ventricular lead system 204 also includes an impedance sense electrode 214 that may be located in the right atrium 220. Alternatively or additionally, an impedance sense electrode 216 may be located in the superior right atrium 220 or near the right atrium 220 within the superior vena cava 222.

A two-electrode impedance sensing configuration is also possible, wherein the right ventricular lead system includes an impedance drive electrode 213 and a tip electrode 212. In this configuration, the tip electrode 212 is used as the impedance sense electrode. Other locations and combinations of impedance sense and drive electrodes are also possible.

In the configuration of FIG. 2, the intracardiac lead system 202 is positioned within the heart 201, with portions of the atrial lead system 205 extending into the right atrium 220 and portions of the right ventricular lead system 204 extending through the right atrium 220 into the right ventricle 218. The A-tip electrode 256 is positioned at an appropriate location within the right atrium 220 for pacing the right atrium 220 and sensing cardiac activity in the right atrium 220. The RV-tip electrode 212 is positioned at an appropriate location within the right ventricle 218 for pacing the right ventricle 218 and sensing cardiac activity in the right ventricle 218.

Additional configurations of sensing, pacing, and defibrillation electrodes can be included in the intracardiac lead system to allow for various sensing, pacing, and defibrillation capabilities of multiple heart chambers. In one configuration, the right ventricular and right atrial leads may include additional electrodes for bipolar sensing and/or pacing, for example. Further, the right ventricular and right atrial leads may also include additional electrodes for cardioversion or defibrillation.

In other configurations, the intracardiac lead system may have only a single lead with electrodes positioned in the right atrium or the right ventricle to implement disordered breathing detection and single chamber cardiac pacing and sensing. In yet other embodiments, the lead system may include intravenous leads that are advanced into the coronary sinus and coronary veins to locate the distal electrode(s) adjacent to the left ventricle or the left atrium. Other lead and electrode arrangements and configurations known in the art are also possible and considered to be within the scope of the present system.

Figure 3:
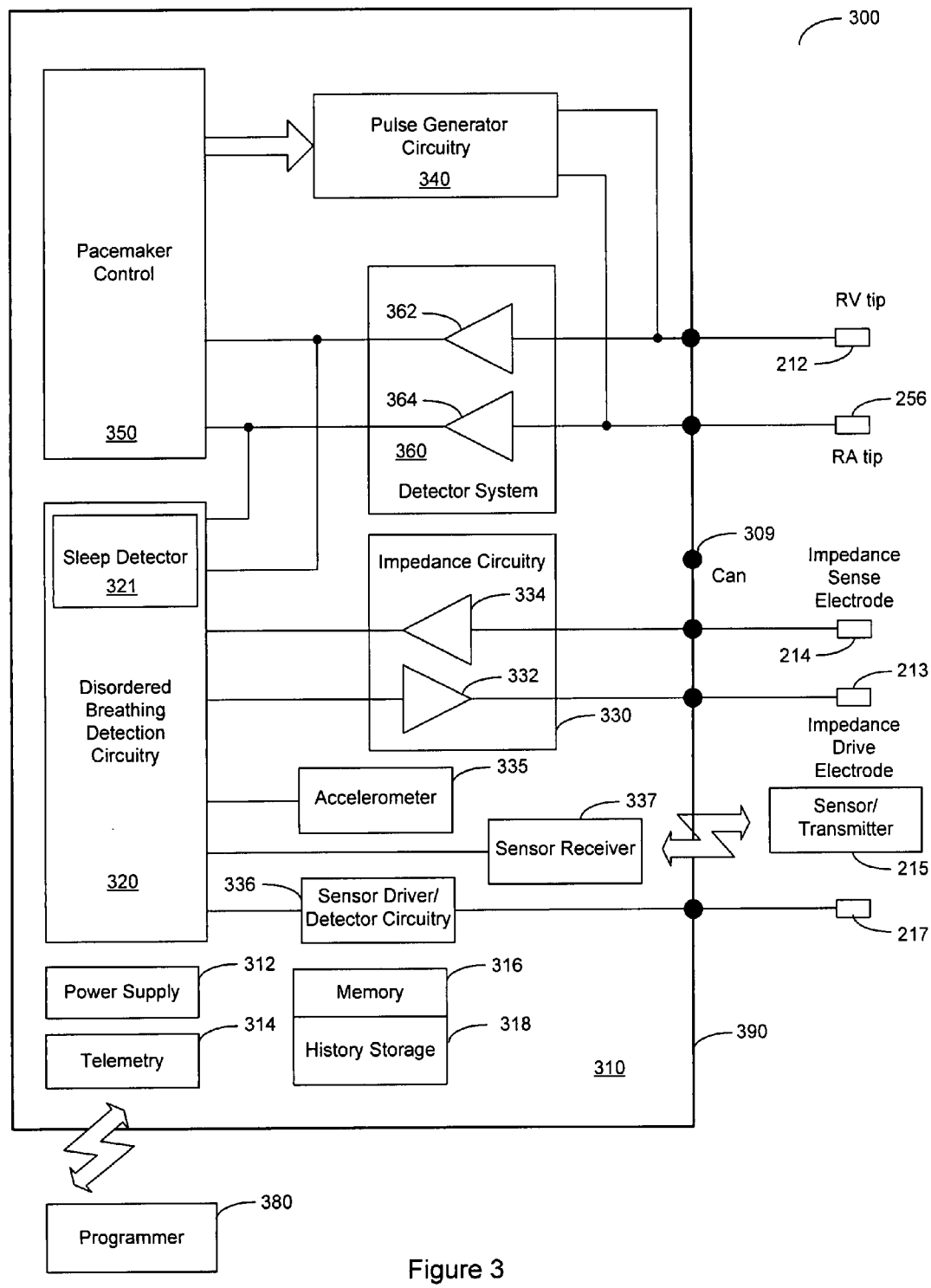
FIG. 3 is a system block diagram of an implantable medical device with which disordered breathing detection may be implemented in accordance with an embodiment of the invention.

Referring now to FIG. 3, there is shown a block diagram of an embodiment of a CRM system 300 configured as a pacemaker and suitable for implementing a disordered breathing detection methodology of the present invention. FIG. 3 shows the CRM 300 divided into functional blocks. It will be understood by those skilled in the art that there exist many possible configurations in which these functional blocks can be arranged and implemented. The example depicted in FIG. 3 is one possible functional arrangement. The CRM 300 includes disordered breathing detection circuitry 320 for receiving signals associated with sleep and/or disordered breathing and detecting disordered breathing in accordance with principles of the invention.

In one embodiment, disordered breathing detection circuitry 320 is incorporated as part of the CRM circuitry 310 encased and hermetically sealed in a housing 390 suitable for implanting in a human body. Power to the CRM 300 is supplied by an electrochemical battery power supply 312 housed within the CRM 300. A connector block (not shown) is additionally attached to the CRM housing 390 to allow for the physical and electrical attachment of the intracardiac lead system conductors to the CRM circuitry 310.

The CRM circuitry 310 may be configured as a programmable microprocessor-based system, with circuitry for detecting disordered breathing in addition to providing pacing therapy to the heart. Cardiac signals may be detected by the detector circuitry 360 and delivered to a pacemaker control system 350. Pace pulses controlled by the pacemaker control 350 and generated by the pulse generator 340 may be delivered to the heart to treat various arrhythmias of the heart.

The memory circuit 316 may store parameters for various device operations involving disordered breathing detection and/or cardiac pacing and sensing. The memory circuit 316 may also store data associated with physiological or other signals received by components of the CRM circuitry 310, such as the impedance drive/sense circuitry 330, the cardiac signal detector system 360, the accelerometer 335, and other circuitry 336, 337 associated with external and/or implantable sensors.

The disordered breathing detection circuitry 320 receives signals derived from the cardiac signal detector system 360, the impedance driver/detector circuitry 330, and the accelerometer 335. The disordered breathing detector 320 may optionally receive signals associated with disordered breathing from additional sensor driver/detector circuitry 336 coupled to one or more additional implantable sensors 217 through a lead system. The disordered breathing detector 320 may optionally receive signals associated with disordered breathing from sensor receiver circuitry 337 coupled to one or more implantable or external sensors 215 through a wireless communication link. Detection of disordered breathing may include detection of sleep onset and termination implemented in sleep detection circuitry 321 according to the principles of the present invention.

Historical data storage 318 may be coupled to the disordered breathing detection circuitry 320 for storing historical data related to disordered breathing. Such data may be transmitted to an external programmer unit 380 and used for various diagnostic or other purposes and as needed or desired.

Telemetry circuitry 314 is coupled to the CRM circuitry 310 to allow the CRM 300 to communicate with an external programmer unit 380. In one embodiment, the telemetry circuitry 314 and the programmer unit 380 use a wire loop antenna and a radio frequency telemetric link to receive and transmit signals and data between the programmer unit 380 and telemetry circuitry 314. In this manner, programming commands and data may be transferred between the CRM circuitry 310 and the programmer unit 380 during and after implant. The programming commands allow a physician to set or modify various parameters used by the CRM. These parameters may include thresholds or indices for use during disordered breathing detection, such as sleep thresholds, disordered breathing indices and parameters, and apnea and hypopnea indices. In addition, the CRM system 300 may download to the programmer unit 380 stored data pertaining to disordered breathing episodes, including the duration, severity, episode respiratory signals, and frequency of the episodes, for example.

Signals associated with patient activity may be detected through the use of an accelerometer 335 that may be positioned within the housing 390 of the CRM 300. The accelerometer responds to patient activity and the accelerometer signal may be correlated with activity level, workload, and/or posture. Signals derived from the accelerometer 335 are coupled to the disordered breathing detection circuitry 320 and may also be used by the pacemaker circuitry 350 for implementing a rate adaptive pacing regimen, for example.

The impedance sense electrode 214, the impedance drive electrode 213, and the impedance driver/detector circuitry 330 are used to measure transthoracic impedance. The transthoracic impedance measurement may be used to calculate various parameters associated with respiration. Under the control of the disordered breathing detection circuitry 320, the impedance driver circuitry 332 produces a current that flows through the blood between the impedance drive electrode 213 and the can electrode 309. The voltage at the impedance sense electrode 214 relative to the can electrode 309 changes as the transthoracic impedance changes. The voltage signal developed between the impedance sense electrode 214 and the can electrode 309 is detected by the impedance sense amplifier 334 located within the impedance driver/detector circuitry 330. This signal may be further filtered, digitized, or otherwise processed within the impedance driver/detector circuitry 330 and delivered to the disordered breathing detection circuitry 320.

Figure 4:
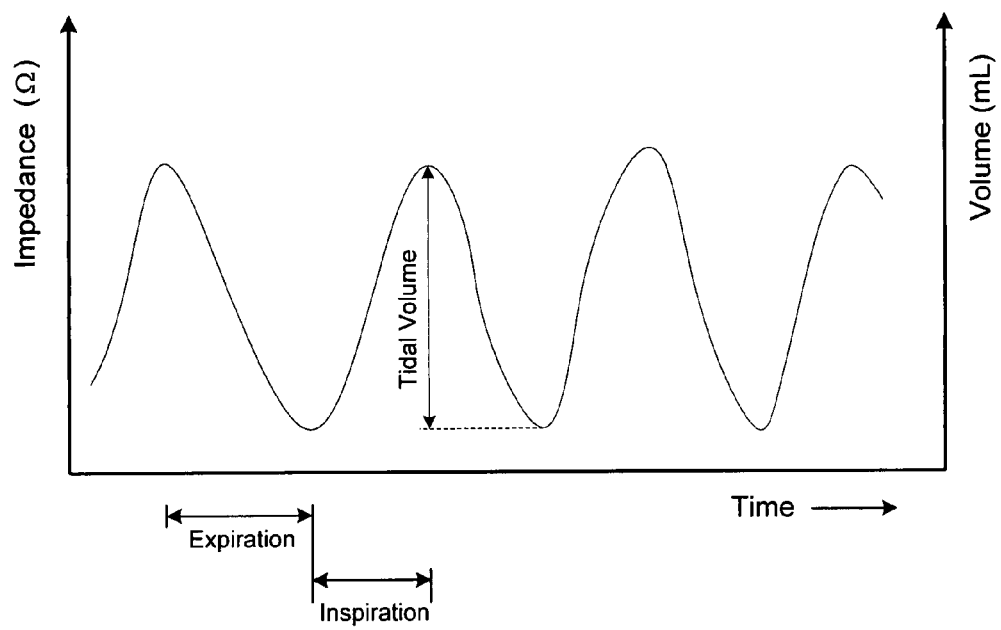
FIG. 4 is a graph of transthoracic impedance used in connection with disordered breathing detection according to an embodiment of the invention.

The voltage signal developed at the impedance sense electrode 214, illustrated in FIG. 4, is proportional to the transthoracic impedance, with the impedance increasing during respiratory inspiration and decreasing during respiratory expiration. The peak-to-peak transition of the impedance measurement is proportional to the amount of air inhaled in one breath, denoted the tidal volume, also illustrated in FIG. 4. The impedance measurement may be further processed to determine the minute ventilation corresponding to the volume of air moved per minute.

Cardiac parameters, including heart rate, heart rate regularity, and QT interval, for example, may also be used in connection with the detection of disordered breathing. Turning back to FIG. 3, cardiac signals are sensed through use of the RV-tip and RA-tip sense electrodes 212, 256. More particularly, the right ventricle signal may be detected as a voltage developed between the RV-tip electrode 212 and the can electrode 309. Right ventricle cardiac signals are sensed and amplified by a right ventricle V-sense amplifier 362 located in the detector system 360. The output of the right ventricle V-sense amplifier 362 may be coupled, for example, to a signal processor and A/D converter within the detector system 360. The processed right ventricle signals may be delivered to the pacemaker control 350 and the disordered breathing detection circuitry 320.

Right atrium cardiac signals are sensed and amplified by a right atrial A-sense amplifier 364 located in the detector system 360. The output of the right atrium A-sense amplifier 364 may be processed by signal processing circuitry and received by the pacemaker control 350 and the disordered breathing detection circuitry 320.

The pacemaker control 350 communicates pacing control signals to the pulse generator circuitry 340 for delivering pacing stimulation pulses to the RV-tip and RA-tip electrodes 212 and 256, respectively, according to a pre-established pacing regimen under appropriate conditions.

In addition to the cardiac, respiration, and activity signals discussed above, additional or alternative signals useful in detection of disordered breathing may be sensed using external and/or implanted sensors 215, 217 and coupled to the disordered breathing detection circuitry 320 through sensor driver/detector and/or sensor receiver circuitry 336, 337. The additional or alternative signals may be used to implement or confirm disordered breathing detection according to the principles of the invention.

Figure 5A:
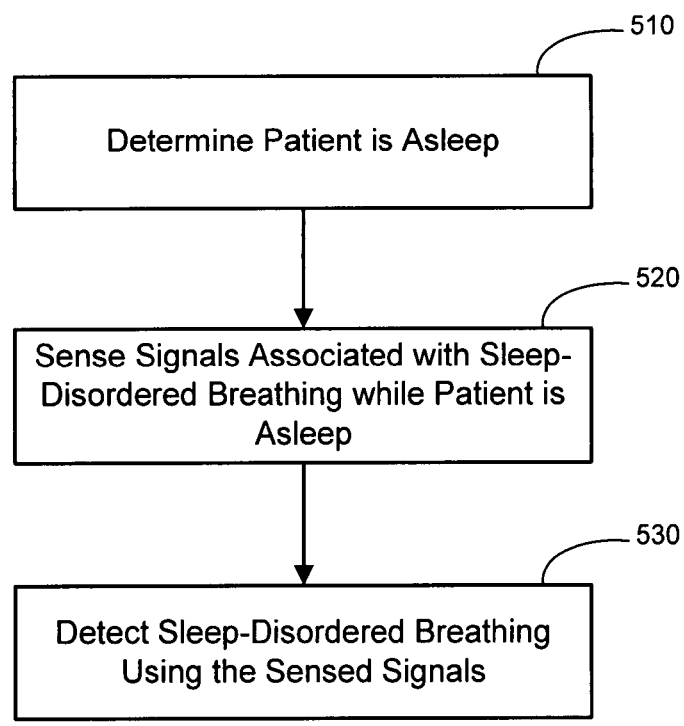
FIGS. 5A-B are flow graphs illustrating methods of detecting disordered breathing according to an embodiment of the invention.

FIG. 5A is a flowchart illustrating a method of detecting disordered breathing in a patient according to an embodiment of the invention. According to this method, disordered breathing may be detected by first determining that the patient has fallen asleep 510. One method of determining sleep involves establishing a sleep threshold associated with a first sleep-related signal. For example, the sleep threshold may be established from analysis of clinical data indicating a sleep threshold using a group of subjects. Alternatively or additionally, the sleep threshold may be established using historical data taken from the particular patient for whom the sleep condition is to be determined.

Sleep may be determined based on a comparison of the first sleep-related signal to the established threshold. For example, if the first sleep-related signal falls below the sleep threshold, sleep onset is determined. If the first sleep-related signal rises above the sleep threshold, sleep termination is determined. As will be understood, sleep onset or termination may be determined based on a signal rising above the sleep threshold or falling below the sleep threshold depending on the nature of the first sleep-related signal and the sleep threshold.

One or more additional sleep-related signals may be used to adjust the sleep threshold. For example, if a sleep-related signal used to adjust the sleep threshold indicates a state incompatible with sleep, for example, a high activity level, the sleep threshold may be adjusted downward to require sensing a decreased level of the first sleep-related signal before a sleep condition is detected.

Alternatively or additionally, sleep may be established based on time of day. Because most patients' sleep patterns are reasonably consistent, establishing sleep based on time of day may be an acceptable technique in some circumstances. Also, an acceptable measurement of the level of sleep-disordered breathing experienced by a patient can be determined using a portion of the patient's sleep period. Thus, only times of day when the patient is likely to be sleeping, e.g., 12 am to 4 am, may need to be used to detect episodes of disordered breathing.

Signals associated with disordered breathing are sensed 520 while the patient is asleep. For example, various cardiac signals and derived parameters, such as heart rate and QT interval, may indicate disordered breathing. Furthermore, respiratory signals and parameters derived from the signals, such as respiratory cycle, minute ventilation, and tidal volume, may indicate disordered breathing. The signals and/or derived parameters associated with disordered breathing may be used to detect sleep disordered breathing 530 according to the principles of the invention.

As previously discussed, the signals associated with sleep and/or disordered breathing may be sensed using sensors that are implanted in the patient, attached externally to the patient, or located in proximity of the patient, for example. The signals may include any signal associated with the condition of sleep or disordered breathing, such as any or all of the representative set of signals and parameters listed above.

Figure 5B:
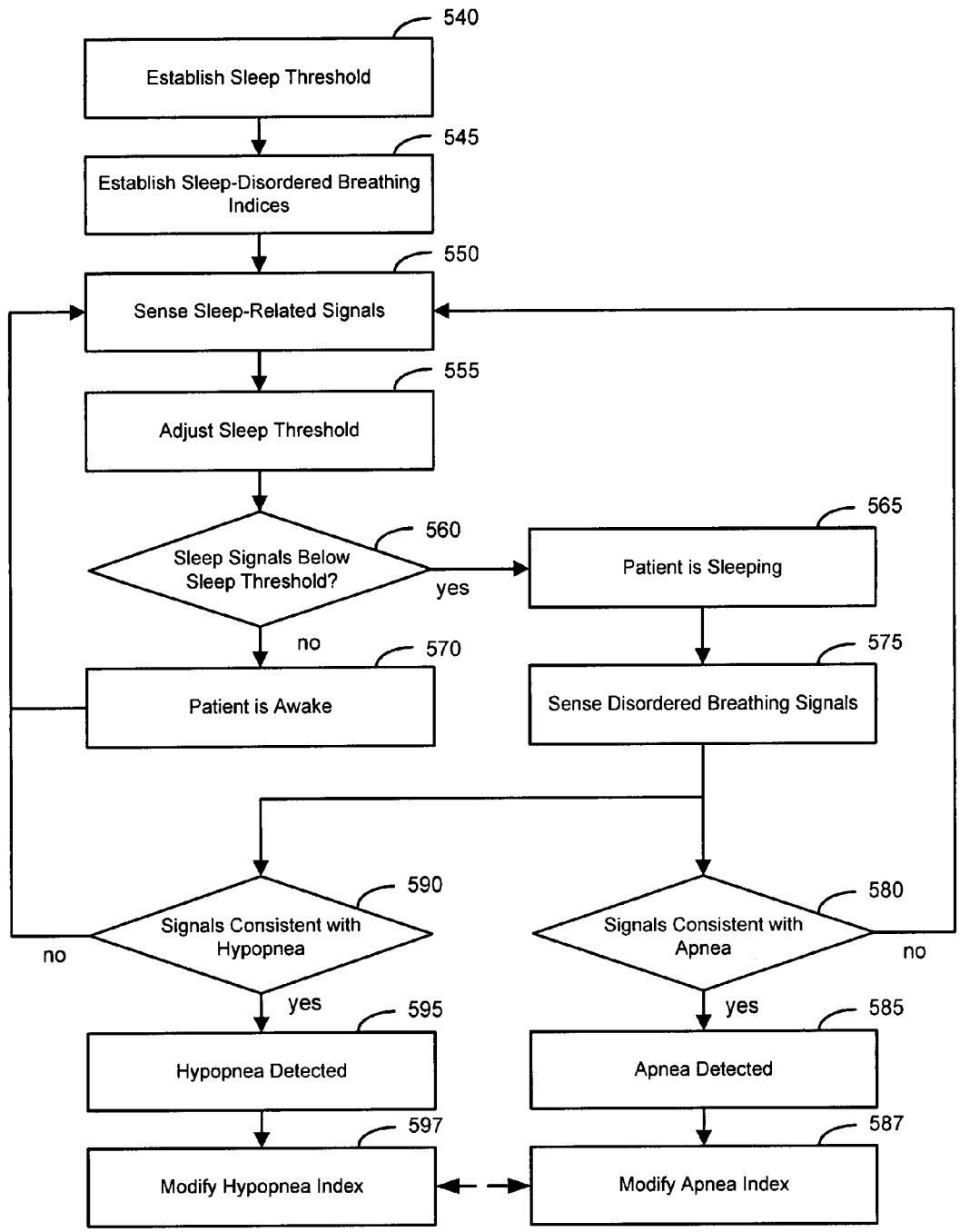

FIG. 5B illustrates a more detailed flow chart of a method for detecting sleep apnea or hypopnea according to the principles of the invention. Prior to detection of disordered breathing episodes, a sleep threshold 540 and disordered breathing indices 545 are established. The sleep threshold and disordered breathing indices may be associated with signals or derived parameters indicative of sleep and/or disordered breathing as listed above. For example, the sleep threshold may be related to patient activity as indicated by the patient's heart rate or the patient's motion sensed by an accelerometer located in or on the patient. Disordered breathing indices may be established using signals associated with disordered breathing and parameters derived from the signals associated with disordered breathing including heart rate, respiration rate, and/or tidal volume, for example. Disordered breathing indices may be used to detect a sleep apnea or hypopnea condition. It will be understood that in some circumstances sleep determination and disordered breathing detection may be implemented using the same signals and/or parameters or different set of signals and/or parameters.

Sleep-related signals, including a first sleep-related signal used to determine the sleep condition, and one or more threshold adjustment sleep-related signals, are sensed 550. The sleep threshold previously established may be adjusted using the one or more threshold adjustment signals 555. So long as the first sleep-related signal exceeds the sleep threshold 560, the patient is determined to be awake 570, and the first sleep-related signal and the threshold adjustment signals continue to be monitored 550. If the first sleep-related signal falls below the sleep threshold 560, an onset of the sleep condition is detected 565.

One or more signals associated with disordered breathing are sensed 575 while the patient is asleep. As previously discussed, these signals may correspond, for example, to cardiac or respiratory parameters such as heart rate, respiration rate, tidal volume, and minute ventilation. The signals associated with disordered breathing are compared 580 to previously established indices corresponding to sleep apnea. If the signals are consistent with sleep apnea, then a sleep apnea condition is detected 585. One or more of the apnea and/or hypopnea indices may be adjusted 587, 597 based on the detected apnea episode.

The signals indicative of disordered breathing are compared 590 to previously established indices corresponding to hypopnea 590. If the signals are consistent with hypopnea, then a hypopnea condition is detected 595. One or more of the apnea and/or hypopnea indices may be adjusted 587, 597 based on the detected hypopnea episode.

The sensitivity of one or more of the apnea or hypopnea indices may be adapted 587, 597 based on characteristics of one or more of the disordered breathing episodes including, for example, the type, duration, severity, and/or frequency of previously detected disordered breathing episodes. For example, detection of a predetermined number of disordered breathing episodes within a selected time period may indicate that additional disordered breathing episodes are likely. Therefore, one or more of the disordered breathing indices may be modified to more quickly detect the next episode of disordered breathing. The sensitivity of these indices may also be adapted based on the patient's cardiopulmonary condition.

Figure 6:
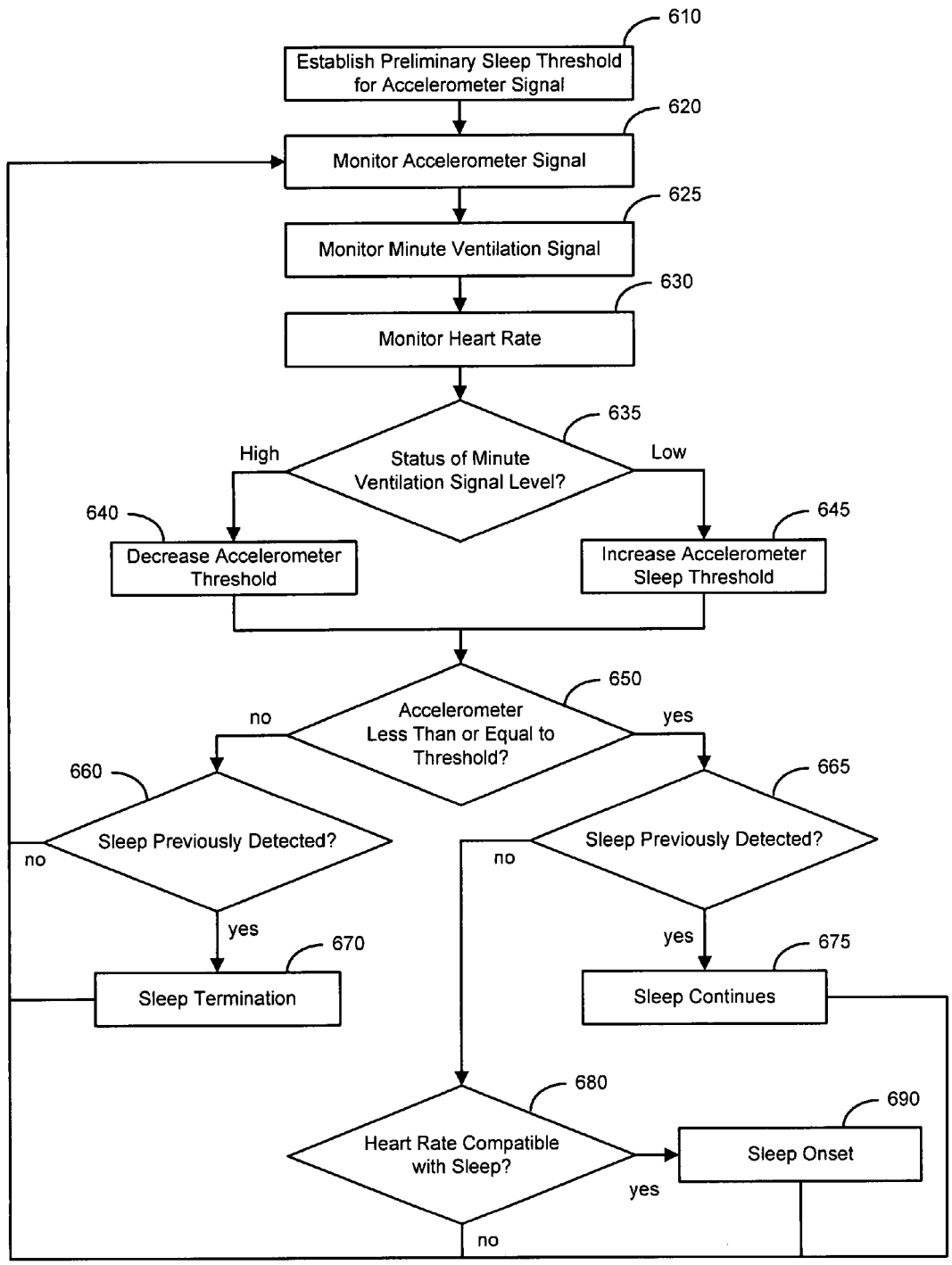
FIG. 6 is a flow graph illustrating a method of sleep detection used in conjunction with detection of disordered breathing according to an embodiment of the invention.

FIG. 6 is a flowchart illustrating a method of sleep detection in accordance with an embodiment of the invention. For the purposes of sleep detection described in relation to FIG. 6, signals using an accelerometer and a minute ventilation sensor are used as the sleep-related signals used for sleep-determination. According to this embodiment, a preliminary sleep threshold is determined 610 for the accelerometer signal. For example, the preliminary sleep threshold may be determined from clinical data taken from a group of subjects or historical data taken from the patient over a period of time.

The activity level of the patient is monitored using an accelerometer 620 that may be incorporated into an implantable cardiac pacemaker as described above. Alternatively, the accelerometer may be attached externally to the patient. The patient's minute ventilation (MV) signal is monitored 625. The MV signal may be derived, for example, using the transthoracic impedance measurement acquired as described above. Transthoracic impedance may be sensed by implantable sensors and the MV signal calculated by an implantable cardiac device. Other methods of determining the MV signal are also possible and are considered to be within the scope of this invention.

In this example, the accelerometer signal represents the first sleep-related signal and is compared with the sleep threshold to detect sleep. The MV signal is the threshold adjustment signal used to adjust the sleep threshold. Additional sleep-related signals, such as heart rate and/or posture may be monitored 630 to confirm sleep.

Threshold adjustment may be accomplished by using the patient's MV signal to moderate the sleep threshold of the accelerometer signal. If the patient's MV signal is low relative to an expected MV level associated with sleep, the accelerometer-based sleep threshold is increased. Similarly, if the patient's MV signal level is high relative to an expected MV level associated with sleep, the accelerometer-based sleep threshold is decreased. Thus, when the patient's MV level is high, a decreased level of activity is required to make the determination that the patient is sleeping. Conversely when the patient's MV level is relatively low, a higher level is required for the sleep determination. The use of at least two sleep-related signals to determine a sleep condition enhances the accuracy of sleep detection over previous methods using only one physiological signal to determine that a patient is sleeping.

Various signal processing techniques may be employed to process the raw sensor signals. For example, a moving average of a plurality of samples of each signal may be calculated and used as the signal. Furthermore, the signals associated with disordered breathing may be filtered and/or digitized. If the MV signal is high 635 relative to an expected MV level associated with sleep, the accelerometer sleep threshold is decreased 640. If the MV signal is low 635 relative to an expected MV level associated with sleep, the accelerometer sleep threshold is increased 645.

If the accelerometer signal is less than or equal to the adjusted sleep threshold 650 and if the patient is not currently in a sleep state 665, then the patient's heart rate is checked 680 to confirm the sleep condition. If the patient's heart rate is compatible with sleep 680, then sleep onset 690 is determined. If the patient's heart rate is incompatible 680 with sleep, then the patient's sleep-related signals continue to be monitored.

If the accelerometer signal is less than or equal to the adjusted sleep threshold 650 and if the patient is currently in a sleep state 665, then a continuing sleep state is determined 675 and the patient's signals associated with disordered breathing continue to be monitored for sleep termination to occur. Additional signals, such as heart rate or body posture, for example, may optionally be monitored to determine the continuation of the sleep state.

If the accelerometer signal is greater than the adjusted sleep threshold 650 and the patient is not 660 currently in a sleep state, then the patient's sleep-related signals continue to be monitored until sleep onset is detected 690. If the accelerometer signal is greater than the adjusted sleep threshold 650 and the patient is 660 currently in a sleep state, then sleep termination is detected 670.

Figure 7A:
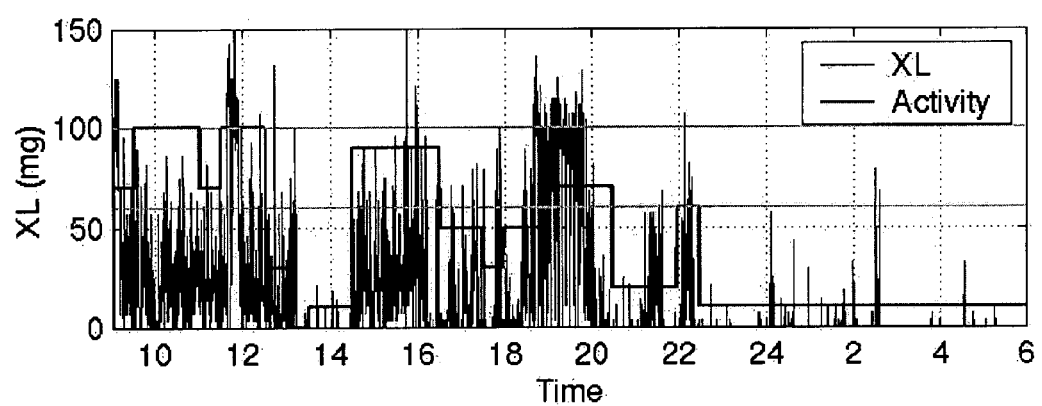
FIG. 7A is a graph of an accelerometer signal indicating patient activity over time that may be used to implement a disordered breathing detection method in accordance with an embodiment of the present invention.
Figure 7B:
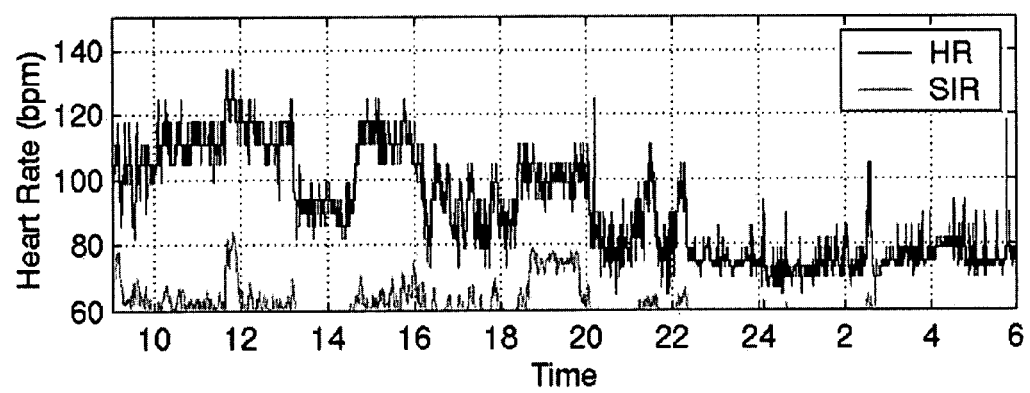
FIG. 7B is a graph of a heart rate signal indicating patient activity over time that may be used to implement a disordered breathing detection method in accordance with an embodiment of the present invention.
Figure 8:
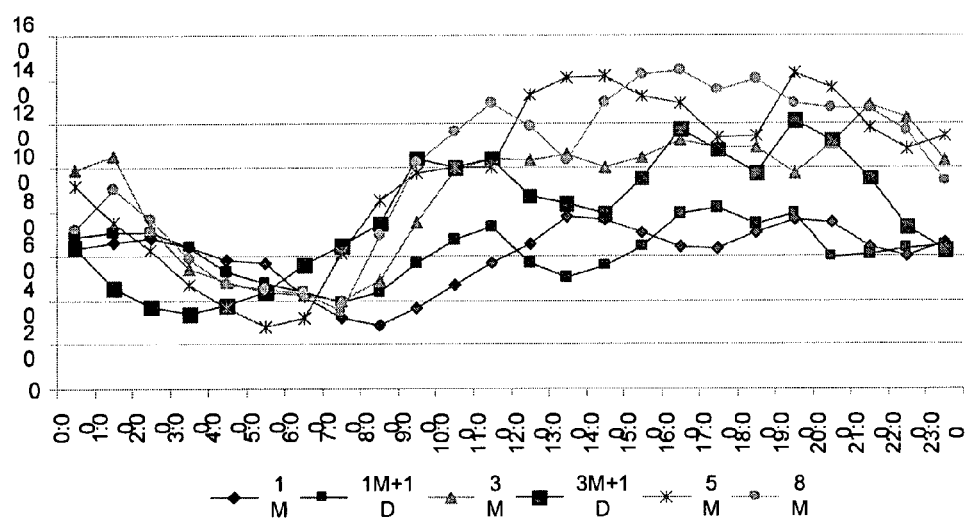
FIG. 8 is a graph of a minute ventilation signal indicating patient respiration that may be used to implement a disordered breathing detection method in accordance with an embodiment of the present invention.
Figure 9:
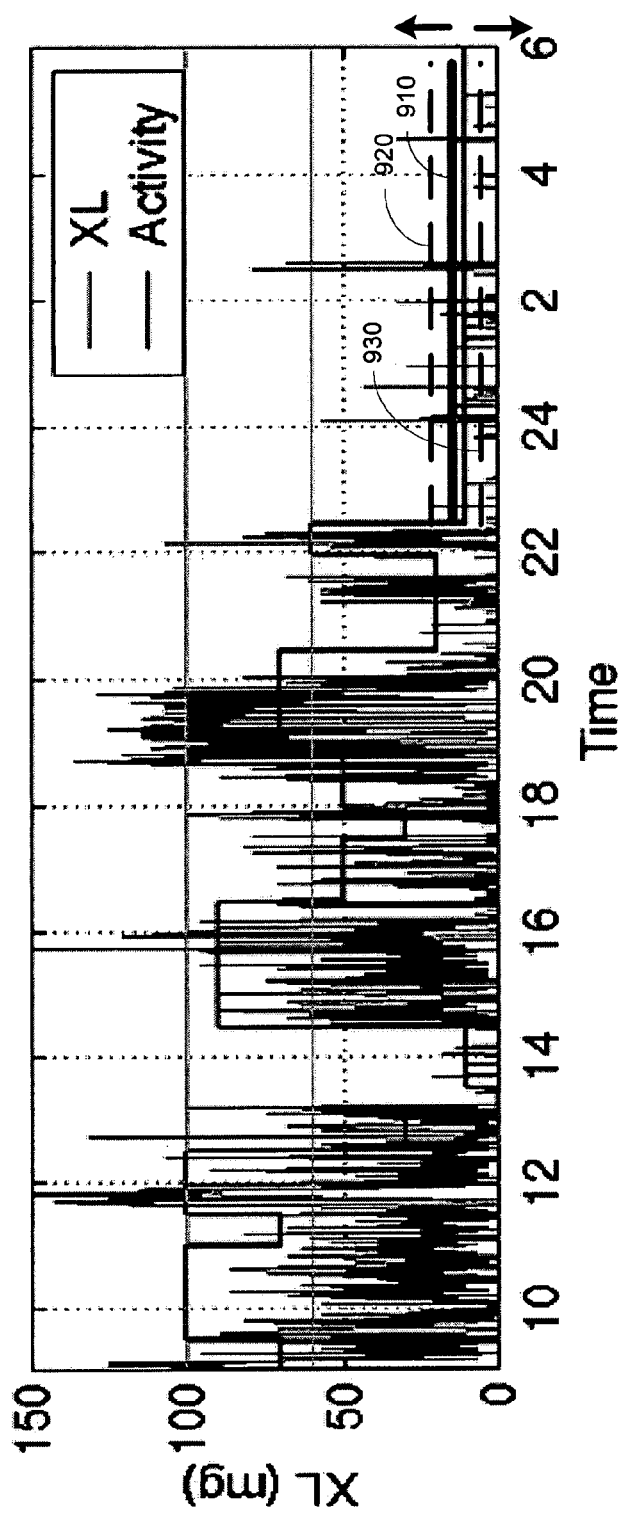
FIG. 9 is a graph illustrating adjustment of an accelerometer sleep threshold using an MV signal in accordance with an embodiment of the invention.

The graphs of FIGS. 7-9 illustrate the adjustment of the accelerometer-based sleep threshold using the MV signal. The relationship between patient activity and the accelerometer and MV signals is trended over a period of time to determine relative signal levels associated with a sleep condition. FIG. 7A illustrates activity as indicated by the accelerometer signal. The patient's heart rate for the same period is graphed in FIG. 7B. The accelerometer signal indicates a period of sleep associated with a relatively low level of activity beginning at slightly before 23:00 and continuing through 6:00. Heart rate appropriately tracks the activity level indicated by the accelerometer indicating a similar period of low heart rate corresponding to sleep. The accelerometer trending is used to establish a preliminary threshold for sleep detection.

FIG. 8 is a graph of baseline trending for an MV signal. Historical data of minute ventilation of a patient is graphed over an 8 month period. The MV signal trending data is used to determine the MV signal level associated with sleep. In this example, a composite MV signal using the historical data indicates a roughly sinusoidal shape with the relatively low MV levels occurring approximately during period from hours 21:00 through 8:00. The low MV levels are associated with periods of sleep.

FIG. 9 illustrates adjustment of the accelerometer-based sleep threshold 910 using the MV signal. FIG. 9 illustrates the accelerometer-based sleep threshold 910 superimposed on the accelerometer signal. As previously discussed, if the patient's MV signal is low relative to an expected MV level associated with sleep, the accelerometer-based sleep threshold 910 is increased 920. If the patient's MV signal level is high relative to an expected MV level associated with sleep, the accelerometer-based sleep threshold is decreased 930. Thus, when the patient's MV level is high, less activity detected by the accelerometer is required to make the determination that the patient is sleeping. If the patient's MV level is relatively low, a higher activity level may result in detection of sleep.

Additional sleep-related signals may be sensed and used to improve the sleep detection mechanism described above. For example, a posture sensor may be incorporated into a pacemaker case and used to detect the posture of the patient. If the posture sensor indicates a vertical posture, then the posture indicator may be used to override a determination of sleep using the accelerometer and MV signals. Other signals may also be used in connection with the confirmation of sleep detection.

Figure 10:
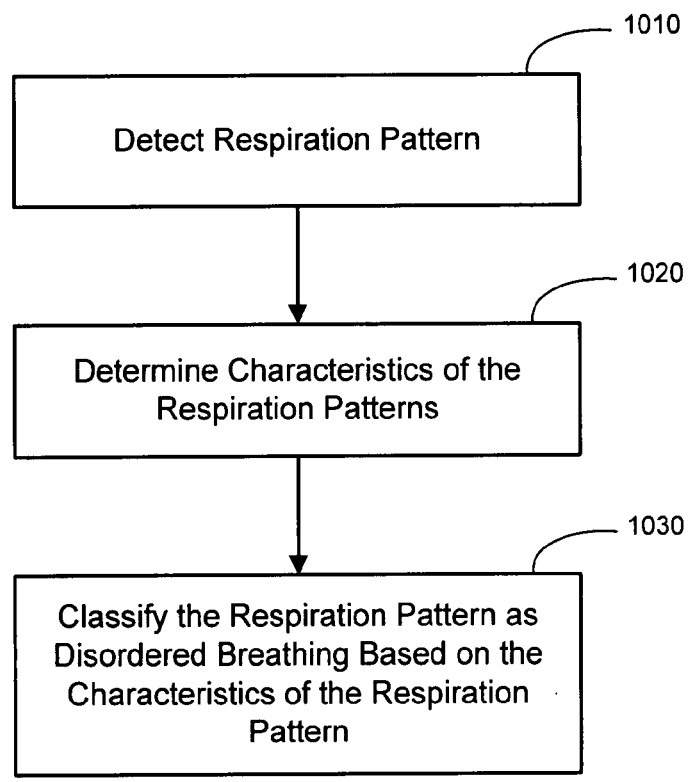
FIG. 10 is a flow graph of a method of detecting disordered breathing according to a method of the invention.

A method of detecting disordered breathing according to another embodiment of the invention is illustrated in the flow chart of FIG. 10. According to this method, signals associated with respiration are sensed and used to detect 1010 a respiration pattern. Characteristics of the respiration pattern are determined 1020. The respiration pattern is classified 1030 as sleep disordered breathing based on the characteristics of the respiration pattern. At least one of detecting the respiration pattern, determining the characteristics of the respiration pattern, and detecting disordered breathing based on characteristics of the respiration pattern is performed at least in part implantably.

Figure 11A:
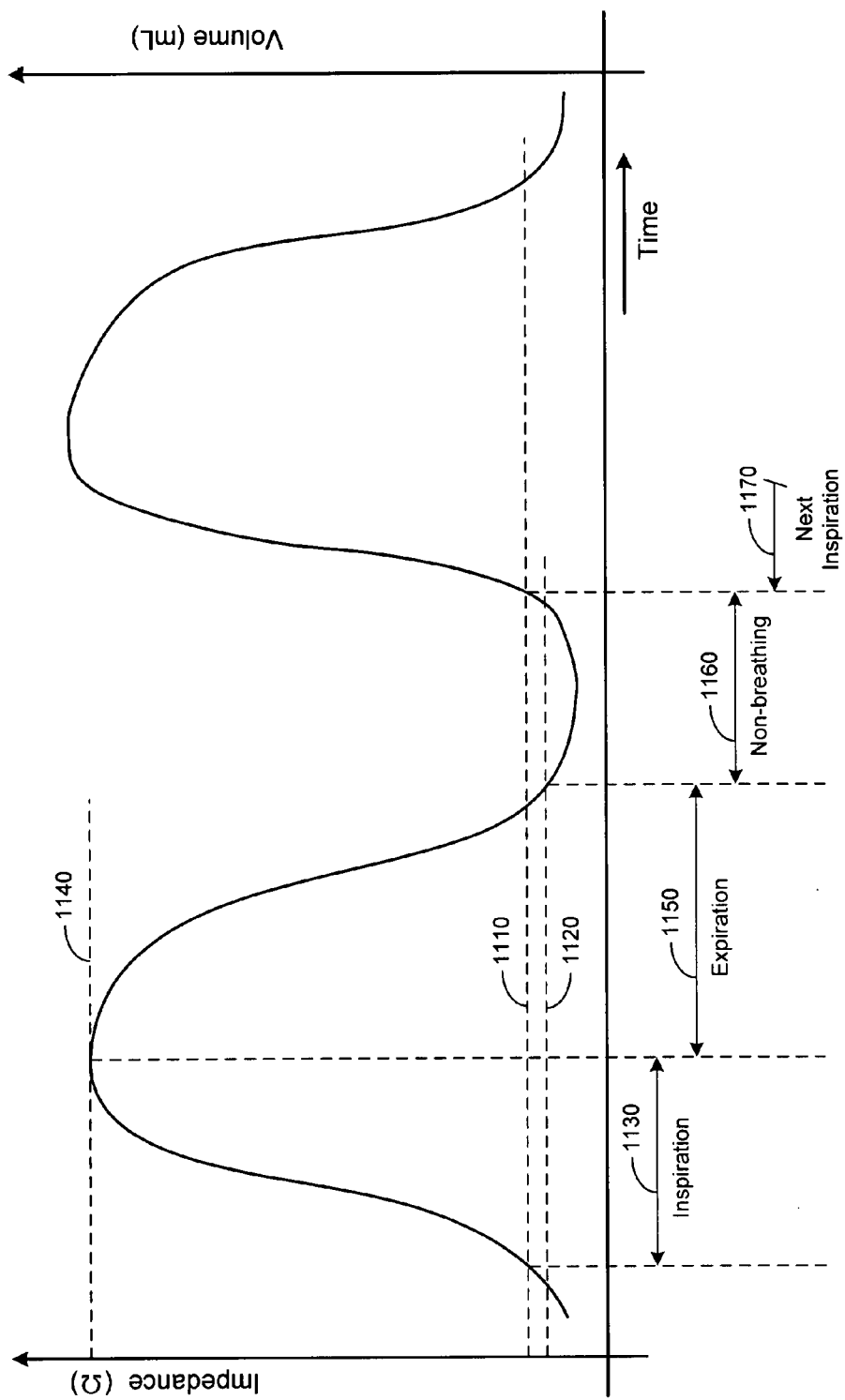
FIGS. 11A-B are graphs of partial respiration patterns illustrating respiration cycle intervals in accordance with a method of the invention.
Figure 11B:
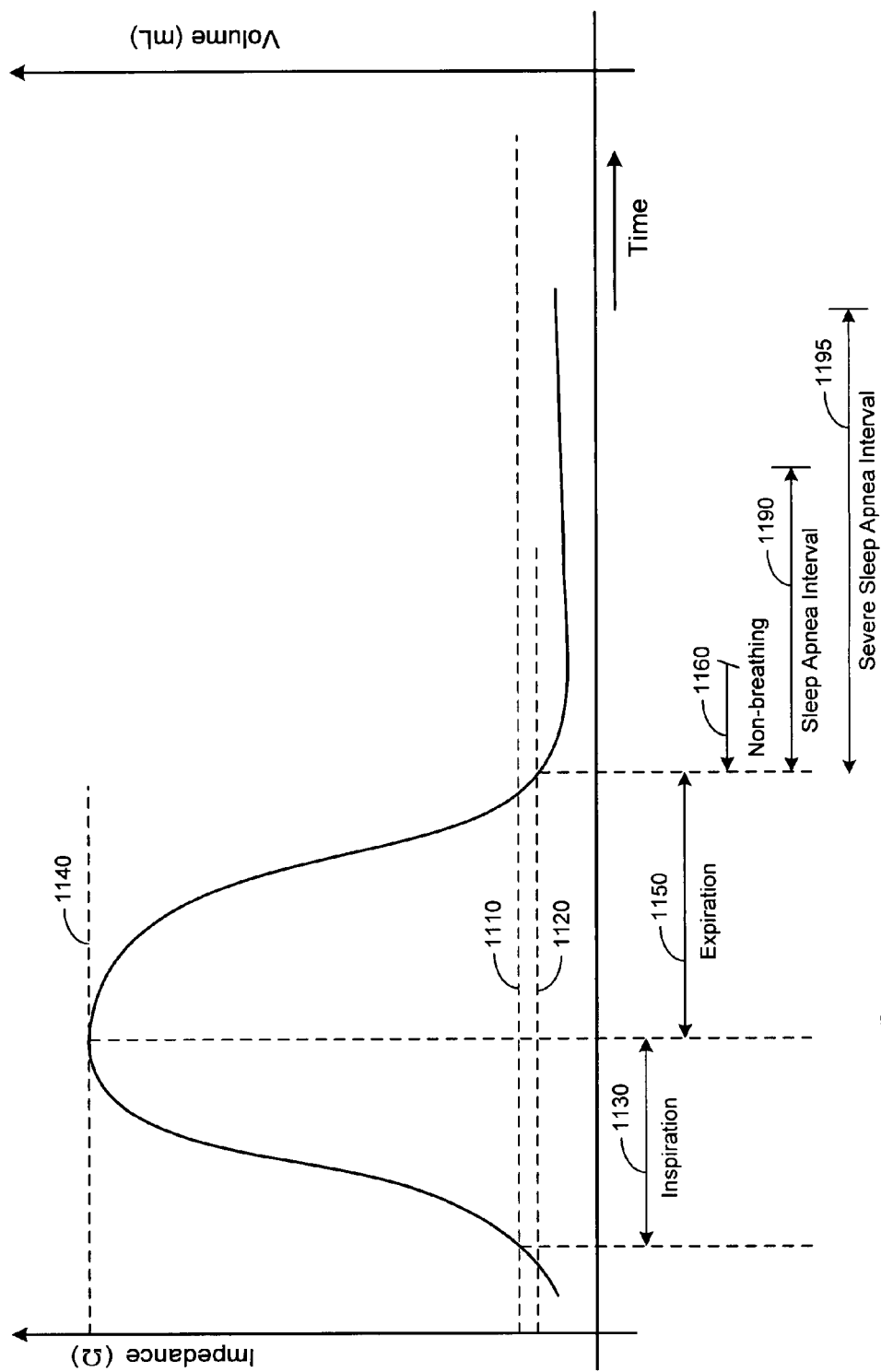

In one configuration, determining the characteristics of the respiration pattern includes determining intervals of the patient's respiration cycles. FIGS. 11A and 11B illustrate portions of a respiration pattern detected using transthoracic impedance measurements acquired as described in more detail above.

FIG. 11A illustrates respiration intervals used for sleep apnea detection according to an embodiment of the invention. A respiration cycle is divided into an inspiration period corresponding to the patient inhaling, an expiration period, corresponding to the patient exhaling, and a non-breathing period occurring between inhaling and exhaling. Respiration intervals are established using inspiration 1110 and expiration 1120 thresholds. The inspiration threshold 1110 marks the beginning of an inspiration period 1130 and is determined by the transthoracic impedance signal rising above the inspiration threshold 1110. The inspiration period 1130 ends when the transthoracic impedance signal is maximum 1140. A maximum transthoracic impedance signal 1140 corresponds to both the end of the inspiration interval 1130 and the beginning of the expiration interval 1150. The expiration interval 1150 continues until the transthoracic impedance falls below an expiration threshold 1120. A non-breathing interval 1160 starts from the end of the expiration period 1150 and continues until the beginning of the next inspiration period 1170.

Detection of sleep apnea and severe sleep apnea according to the principles of the invention are illustrated in FIG. 11B. The patient's respiration signals are monitored and the respiration cycles are defined according to inspiration 1130, expiration 1150, and non-breathing 1160 intervals as described in connection with FIG. 11A. A condition of sleep apnea is detected when a non-breathing period 1160 exceeds a first predetermined interval 1190, denoted the sleep apnea interval. A condition of severe sleep apnea is detected when the non-breathing period 1160 exceeds a second predetermined interval 1195, denoted the severe sleep apnea interval. For example, sleep apnea may be detected when the non-breathing interval exceeds about 10 seconds, and severe sleep apnea may be detected when the non-breathing interval exceeds about 20 seconds.

Figure 12A:
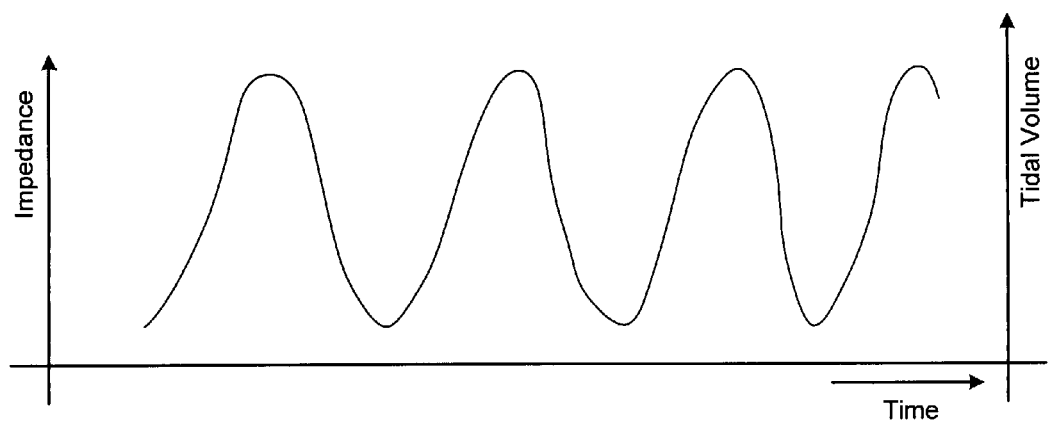
FIGS. 12A-B are graphs illustrating normal and disordered respiration patterns.
Figure 12B:
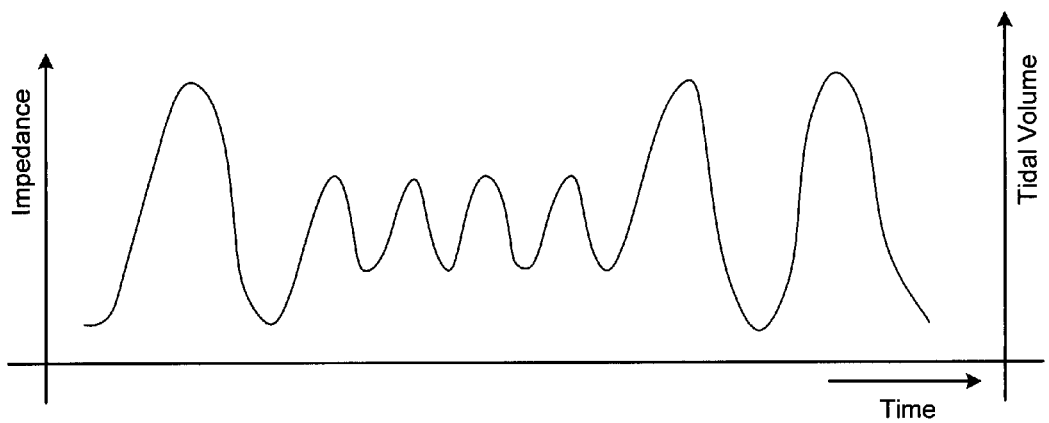

Hypopnea is a condition of disordered breathing characterized by abnormally shallow breathing. FIGS. 12A-B are graphs of tidal volume derived from transthoracic impedance measurements that compare the tidal volume of a normal breathing cycle to the tidal volume of a hypopnea episode. FIG. 12A illustrates normal respiration tidal volume and rate. As shown in FIG. 12B, hypopnea involves a period of very shallow respiration at an otherwise normal rate.

According to an embodiment of the invention, hypopnea is detected by comparing a patient's respiratory tidal volume to a hypopnea tidal volume index. The tidal volume for each respiration cycle is derived from transthoracic impedance measurements acquired in the manner described above. The hypopnea tidal volume index may be established using clinical results providing a representative tidal volume and duration of hypopnea events. In one configuration, hypopnea is detected when an average of the patient's respiratory tidal volume taken over a selected time interval falls below the hypopnea tidal volume index. Furthermore, various combinations of hypopnea cycles and non-breathing intervals may be used to detect hypopnea, where the non-breathing intervals are determined as described above.

Figure 13:
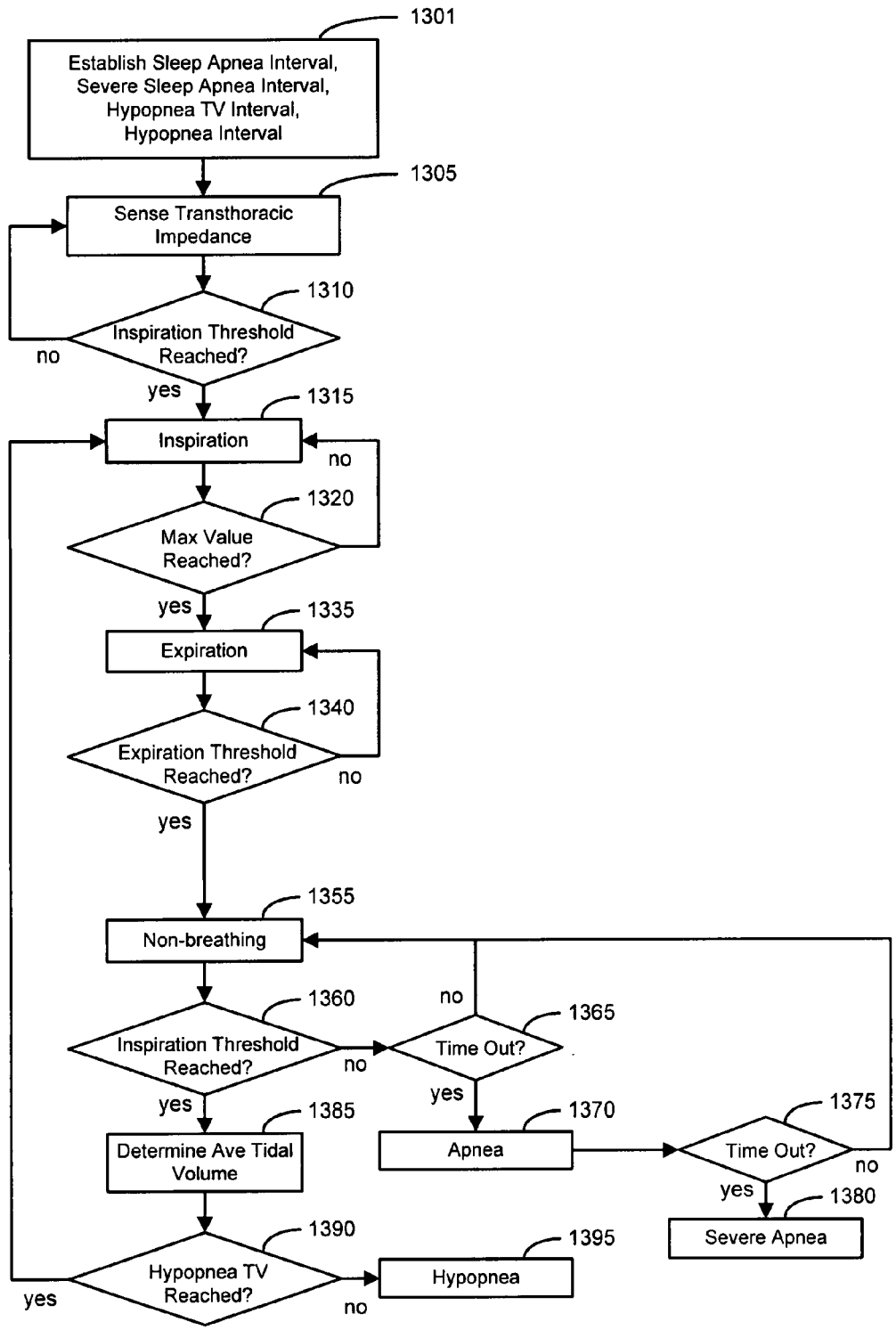
FIG. 13 is a flow graph of a method of detecting disordered breathing according to a method of the invention.

FIG. 13 is a flow chart illustrating a method of apnea and/or hypopnea detection according to principles of the invention. Various parameters are established 1301 before analyzing the patient's respiration for disordered breathing episodes, including, for example, inspiration and expiration thresholds, sleep apnea interval, severe sleep apnea interval, and hypopnea tidal volume index.

The patient's transthoracic impedance is measured 1305 as described in more detail above. If the transthoracic impedance exceeds 1310 the inspiration threshold, the beginning of an inspiration interval is detected 1315. If the transthoracic impedance remains below 1310 the inspiration threshold, then the impedance signal is checked 1305 periodically until inspiration 1315 occurs.

During the inspiration interval, the patient's transthoracic impedance is monitored until a maximum value of the transthoracic impedance is detected 1320. Detection of the maximum value signals an end of the inspiration period and a beginning of an expiration period 1335.

The expiration interval is characterized by decreasing transthoracic impedance. When the transthoracic impedance falls below 1340 the expiration threshold, a non-breathing interval is detected 1355.

If the transthoracic impedance does not exceed 1360 the inspiration threshold within a first predetermined interval 1365, denoted the sleep apnea interval, then a condition of sleep apnea is detected 1370. Severe sleep apnea is detected 1380 if the non-breathing period extends beyond a second predetermined interval 1375, denoted the severe sleep apnea interval.

When the transthoracic impedance exceeds 1360 the inspiration threshold, the tidal volume from the peak-to-peak transthoracic impedance is calculated, along with a moving average of past tidal volumes 1385. The peak-to-peak transthoracic impedance provides a value proportional to the tidal volume of the respiration cycle. This value is compared 1390 to a hypopnea tidal volume index. If the peak-to-peak transthoracic impedance is consistent with 1390 the hypopnea tidal volume index, then a hypopnea cycle is detected 1395. If a series of hypopnea cycles are detected, a hypopnea episode is detected.

Additional sensors, such as motion sensors and/or posture sensors, may be used to confirm or verify the detection of a sleep apnea or hypopnea episode. The additional sensors may be employed to prevent false or missed detections of sleep apnea/hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern is detected as a disordered breathing episode based on the comparison.

Figure 14:
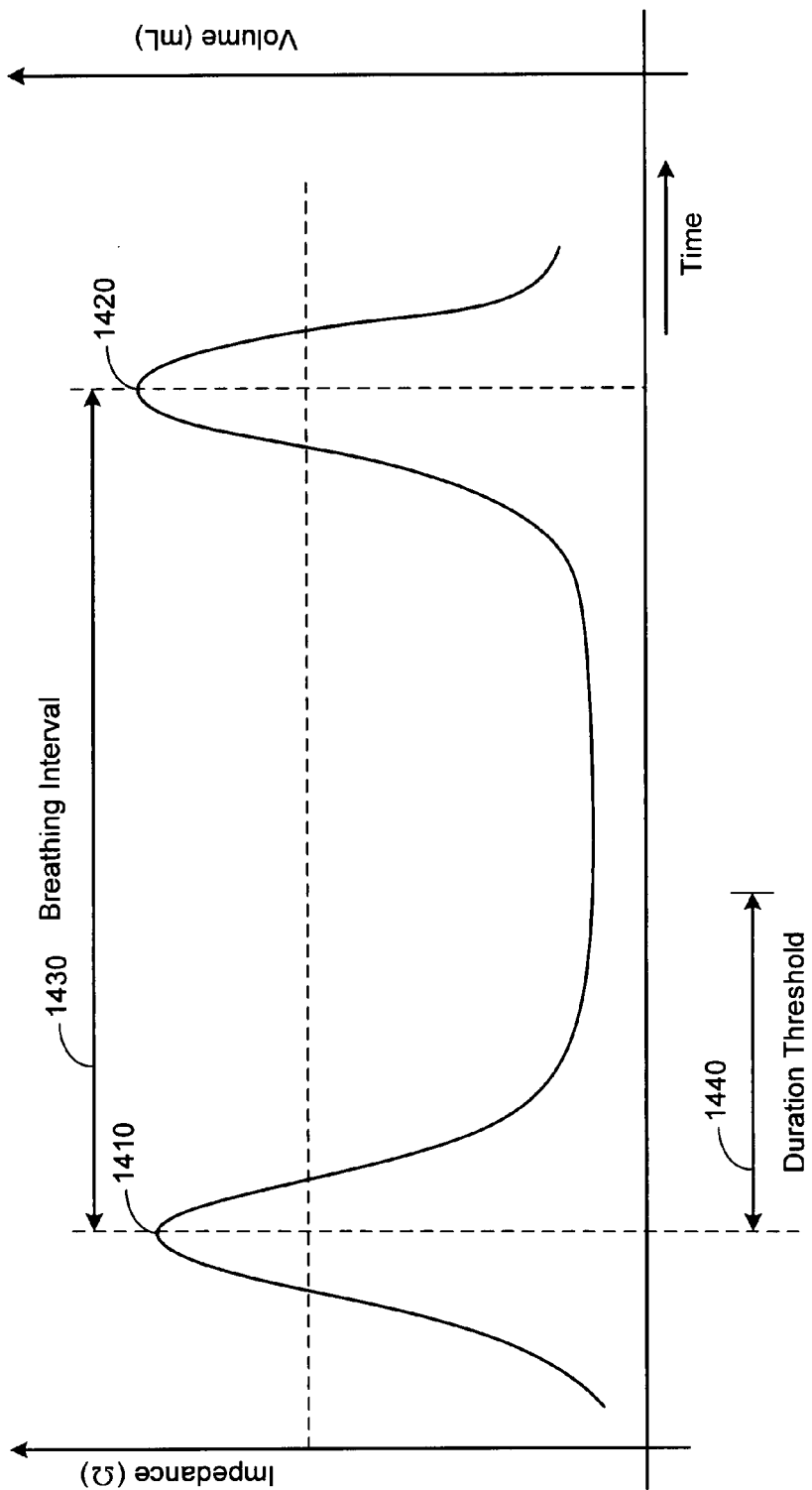
FIG. 14 is a graph of a respiration signal illustrating a breathing interval and a duration threshold in accordance with an embodiment of the invention.

According to principles of the invention, a breath interval 1430 is established for each respiration cycle. A breath interval represents the interval of time between successive breaths, as illustrated in FIG. 14. A breath interval 1430 may be defined in a variety of ways, for example, as the interval of time between successive maxima 1410, 1420 of the impedance signal waveform.

Detection of disordered breathing, in accordance with methods of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 14. Apnea represents a period of non-breathing. A breath interval 1430 exceeding a duration threshold 1440, comprises an apnea episode.

Hypopnea may be detected using the duration threshold and tidal volume threshold. A hypopnea event represents a period of shallow breathing. Each respiration cycle in a hypopnea event is characterized by a tidal volume less than the tidal volume threshold. Further, the hypopnea event involves a period of shallow breathing greater than the duration threshold.

Figure 15:
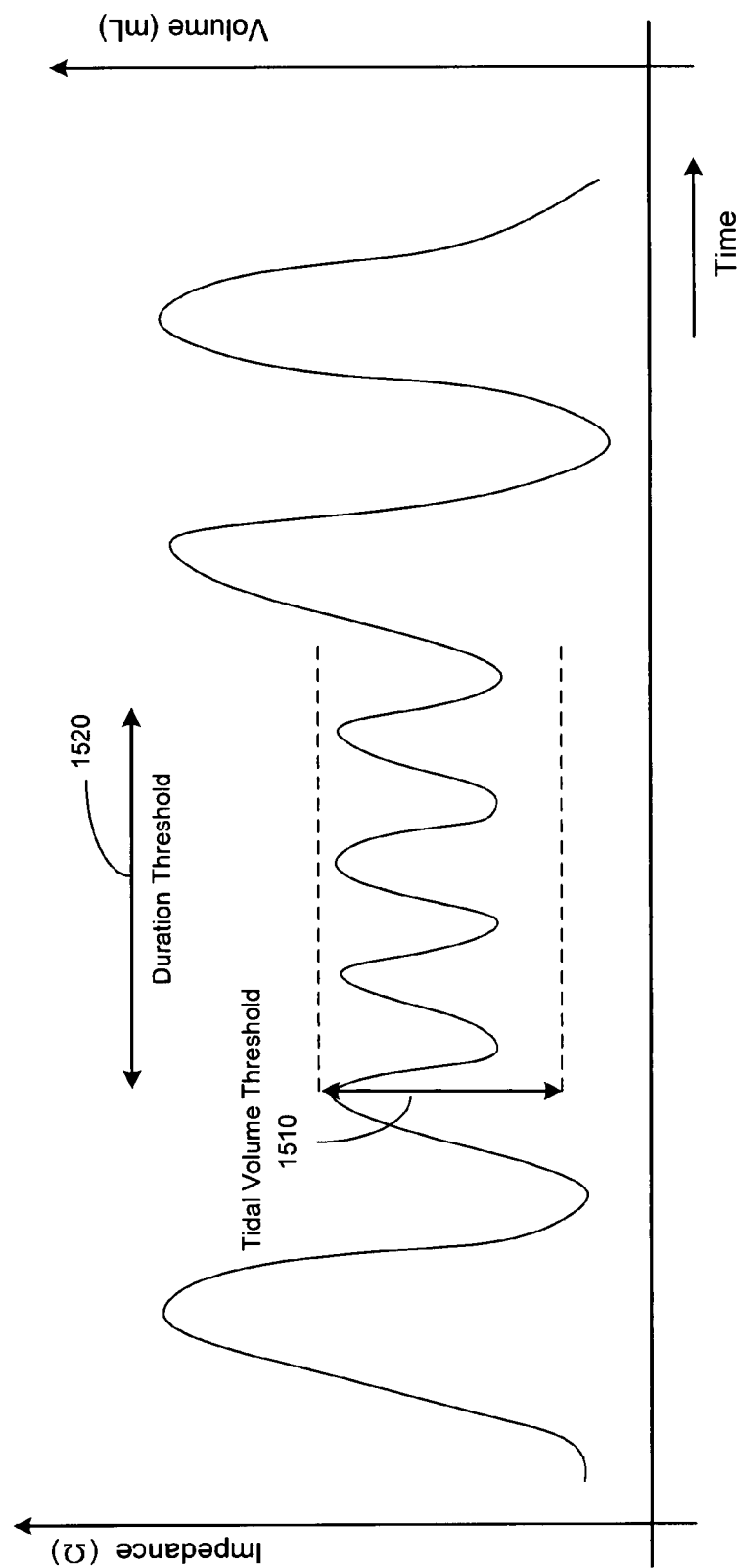
FIG. 15 is a graph of a respiration signal illustrating a duration threshold and a tidal volume threshold in accordance with an embodiment of the invention.

Hypopnea detection in accordance with an embodiment of the invention is illustrated in FIG. 15. Shallow breathing is detected when the tidal volume of one or more breaths is below a tidal volume threshold 1510. If the shallow breathing continues for an interval greater than a duration threshold 1520, then the breathing pattern represented by the sequence of shallow respiration cycles, is classified as a hypopnea event.

Figures 16A, 16B, 16C, 16D, 16E:
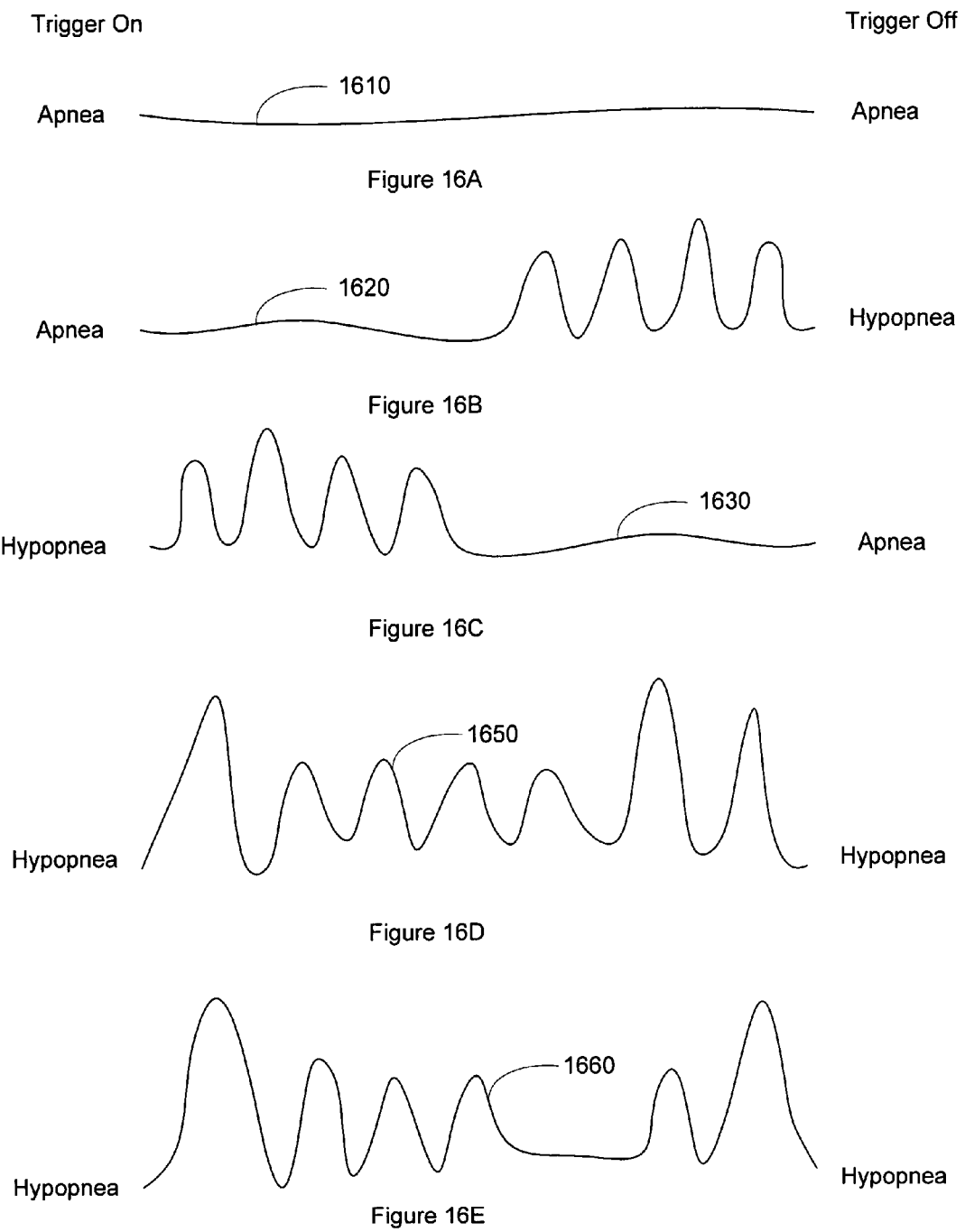
FIGS. 16A-E illustrate respiration patterns that may be classified as disordered breathing episodes in accordance with an embodiment of the invention.

Disordered breathing events may comprise a mixture of apnea and hypopnea respiration cycles. As illustrated in FIGS. 16A-E, a respiration pattern detected as a disordered breathing episode may include only an apnea respiration cycle 1610 (FIG. 16A), only hypopnea respiration cycles 1650 (FIG. 16D), or a mixture of hypopnea and apnea respiration cycles 1620 (FIG. 16B), 1630 (FIG. 16C), 1660 (FIG. 16E). A disordered breathing event 1620 may begin with an apnea respiration cycle and end with one or more hypopnea cycles. In another pattern, the disordered breathing event 1630 may begin with hypopnea cycles and end with an apnea cycle. In yet another pattern, a disordered breathing event 1660 may begin and end with hypopnea cycles with an apnea cycle in between the hypopnea cycles.

Figure 17:
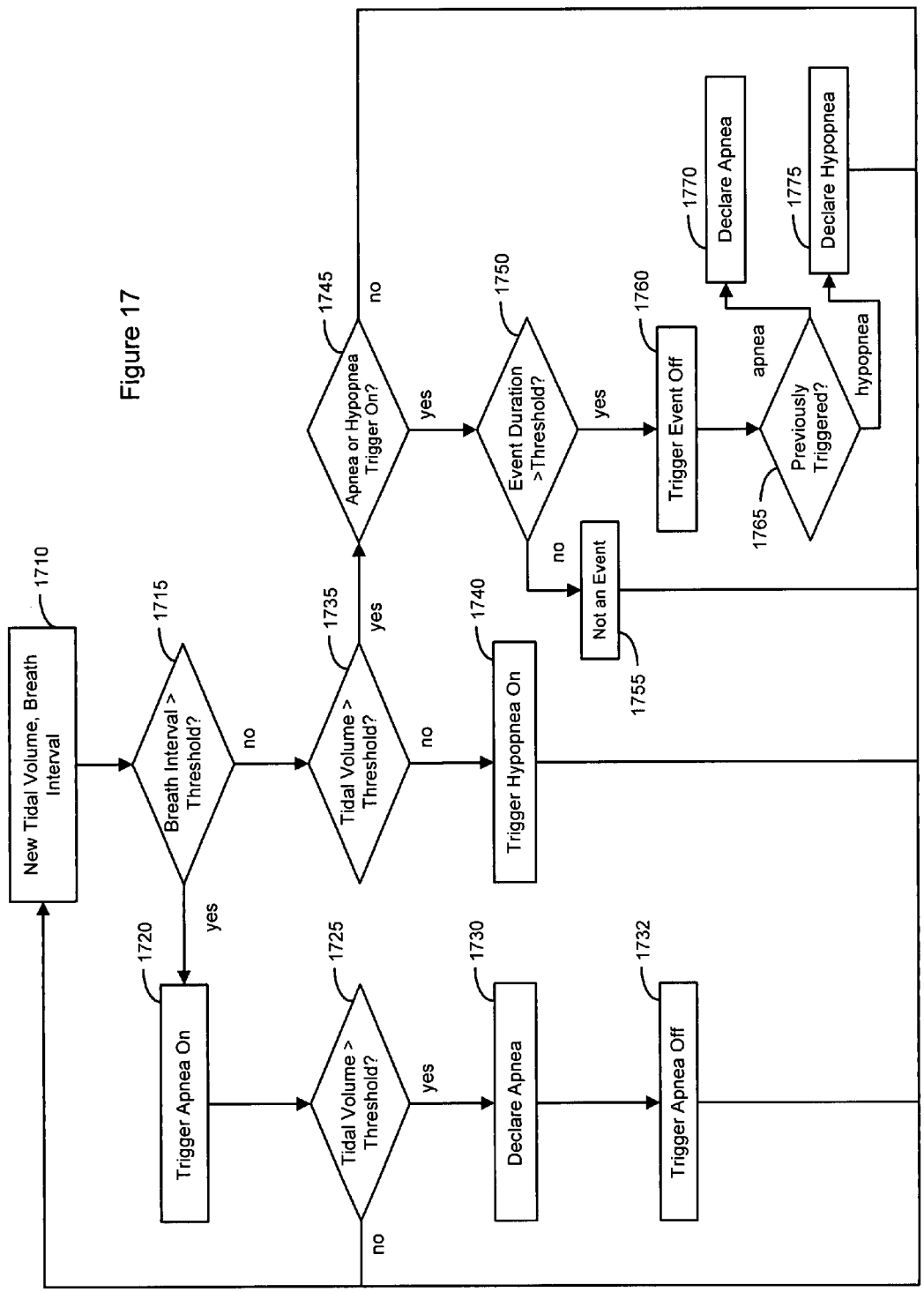
FIG. 17 is a flow graph of a method of detecting disordered breathing in accordance with an embodiment of the invention.

FIG. 17 is a flow chart of a method for detecting disordered breathing by classifying breathing patterns using breath intervals in conjunction with tidal volume and duration thresholds as described in connection with FIGS. 14-16 above. In this example, a duration threshold and a tidal volume threshold are established for determining both apnea and hypopnea breath intervals. An apnea episode is detected if the breath interval exceeds the duration threshold. A hypopnea episode is detected if the tidal volume of successive breaths remains less than the tidal volume threshold for a period in excess of the duration threshold. Mixed apnea/hypopnea episodes may also occur. In these cases, the period of disordered breathing is characterized by shallow breaths or nonbreathing intervals. During the mixed apnea/hypopnea episodes, the tidal volume of each breath remains less than the tidal volume threshold for a period exceeding the duration threshold.

Transthoracic impedance is sensed and used to determine the patient's respiration cycles. Each breath 1710 is characterized by a breath interval, i.e., the interval of time between two impedance signal maxima and a tidal volume (TV).

If a breath interval exceeds 1715 the duration threshold, then the respiration pattern is consistent with an apnea event, and an apnea event trigger is turned on 1720. If the tidal volume of the breath interval exceeds 1725 the tidal volume threshold, then the breathing pattern is characterized by two respiration cycles of normal volume separated by a non-breathing interval. This pattern represents a purely apneic disordered breathing event, and apnea is detected 1730. Because the final breath of the breath interval was normal, the apnea event trigger is turned off 1732, signaling the end of the disordered breathing episode. However, if the tidal volume of the breath interval does not exceed 1725 the tidal volume threshold, the disordered breathing period is continuing and the next breath is checked 1710.

If the breath interval does not exceed 1715 the duration threshold, then the tidal volume of the breath is checked 1735. If the tidal volume does not exceed 1735 the tidal volume threshold, the breathing pattern is consistent with a hypopnea cycle and a hypopnea event trigger is set on 1740. If the tidal volume exceeds the tidal volume threshold, then the breath is normal.

If a period of disordered breathing is in progress, detection of a normal breath signals the end of the disordered breathing. If disordered breathing was previously detected 1745, and if the disordered breathing event duration has extended for a period of time exceeding 1750 the duration threshold, and the current breath is normal, then the disordered breathing trigger is turned off 1760. In this situation, the duration of the disordered breathing episode was of sufficient duration to be classified as a disordered breathing episode. If an apnea event was previously triggered 1765, then an apnea event is declared 1770. If a hypopnea was previously triggered 1765, then a hypopnea event is declared 1775.

If disordered breathing was previously detected, but the duration of the disordered breathing episode did not extend for a period of time exceeding 1750 the duration threshold, then the period of disordered breathing was not of sufficient duration to be classified as a disordered breathing episode 1755.

Although the specific examples of disordered breathing provided above involve types of disordered breathing that generally occur while a person is asleep, disordered breathing may also occur while a person is awake. Waking disordered breathing is frequently associated with compromised cardiopulmonary function caused by congestive heart failure. Examples of the types of disordered breathing that may occur while a person is awake include, for example, periodic breathing and Cheyne-Stokes breathing.

Periodic breathing involves successive periods of regular respiration followed by apneic periods. Although periodic breathing is more frequent during sleep, it can also occur while the patient is awake. Cheyne-Stokes breathing is another example of a wake-disordered breathing condition. Cheyne-Stokes breathing is characterized by rhythmic increases and decreases in the tidal volume of breaths and breathing frequency. Cheyne-Stokes breathing particularly affects patients who have heart problems, such as congestive heart failure, or nervous disorders, such as those caused by a stroke.

The methods, devices, and systems of the invention described herein are particularly well-suited for detecting sleep-disordered breathing, such as apnea and hypopnea. However, the principles of the invention are also applicable to implement detection of disordered breathing episodes that occur while the patient is awake. Characteristics of detected respiration patterns may be determined and used to detect wake-disordered breathing episodes such as Cheyne-Stokes and periodic breathing. By the methods of the invention, one or more disordered breathing indices indicative of wake-disordered breathing may be established and compared with respiration signals to detect episodes of wake-disordered breathing.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for detecting sleep-disordered breathing of a patient, comprising:
   detecting a respiration pattern of one or more respiration cycles;
   determining characteristics of the respiration pattern, comprising:
      determining one or more breath intervals and one or more tidal volume measurements of the one or more respiration cycles;
      identifying an ongoing disordered breathing event as one or both of an apnea event and a hypopnea event based on comparison of the breath intervals to a breath interval threshold or the tidal volume measurements to a tidal volume threshold; and
      determining a duration of the ongoing disordered breathing event; and
   if the ongoing disordered breathing duration exceeds an event duration threshold, discriminating between apnea, hypopnea and mixed apnea and hypopnea based on the one or more characteristics of the respiration pattern, wherein at least one of detecting, determining and discriminating is performed at least in part implantably.

2. The method of claim 1, further comprising determining that the patient is asleep.

3. The method of claim 1, wherein at least two of detecting, determining, and classifying is performed at least in part implantably.

4. The method of claim 1, wherein at each of detecting, determining, and classifying is performed at least in part implantably.

5. The method of claim 1, wherein detecting a respiration pattern comprises measuring transthoracic impedance.

6. The method of claim 1, further comprising
   establishing one or both of the breath interval threshold or the tidal volume threshold for a particular patient.

7. The method of claim 6, wherein establishing the breath interval threshold or the tidal volume threshold comprises modifying the breath interval threshold or the tidal volume threshold based on a condition of the patient.

8. The method of claim 7, wherein the condition of the patient comprises a cardiopulmonary disease condition.

9. The method of claim 6, further comprising adapting a sensitivity of the breath interval threshold or the tidal volume threshold based on one or more previously detected episodes of sleep-disordered breathing.

10. The method of claim 9, wherein adapting the sensitivity of the breath interval threshold or the tidal volume threshold comprises adapting the sensitivity based on a frequency of the one or more previously detected episodes of sleep-disordered breathing.

11. The method of claim 9, wherein adapting the sensitivity of the breath interval threshold or the tidal volume threshold comprises adapting the sensitivity based on a severity of the one or more previously detected episodes of sleep-disordered breathing.

12. The method of claim 9, wherein adapting the sensitivity of the breath interval threshold or the tidal volume threshold comprises adapting the sensitivity based on an interval between two or more previously detected episodes of sleep-disordered breathing.

13. The method of claim 1, wherein:
determining the one or more characteristics of the respiration pattern comprises determining a tidal volume of each respiration cycle and a duration of the respiration pattern; and
classifying the respiration pattern as sleep-disordered breathing comprises classifying the respiration pattern as hypopnea by comparing the tidal volume of each respiration cycle to a tidal volume index and comparing the duration of the respiration pattern to a predetermined duration threshold.

14. The method of claim 1, wherein:
determining the one or more characteristics of the respiration pattern comprises determining a breathing interval; and
classifying the respiration pattern as sleep-disordered breathing comprises classifying the respiration pattern as apnea by comparing the breathing interval to a predetermined duration threshold.

15. The method of claim 1, further comprising storing information about the sleep-disordered breathing.

16. The method of claim 1, further comprising displaying information about the sleep-disordered breathing.

17. A method for detecting disordered breathing of a patient, comprising:
detecting a respiration pattern of one or more respiration cycles;
determining characteristics of the respiration pattern, comprising:
determining one or more breath intervals and one or more tidal volume measurements of the one or more respiration cycles;
identifying an ongoing disordered breathing event as one or both of an apnea event and a hypopnea event based on a comparison of the breath intervals to a breath interval threshold or the tidal volume measurement to a tidal volume threshold; and
determining a duration of the ongoing disordered breathing event; and if the ongoing disordered breathing duration exceeds an event duration threshold, discriminating between apnea, hypopnea and mixed apnea and hypopnea based on the one or more characteristics of the respiration pattern, wherein at least one of detecting, determining and discriminating is performed at least in part implantably.

18. The method of claim 17, wherein detecting the respiration pattern comprises detecting the respiration pattern while the patient is awake.

19. The method of claim 17, wherein detecting the respiration pattern comprises measuring transthoracic impedance.

20. The method of claim 17, further comprising establishing one or both of the breath interval threshold and the tidal volume threshold for a particular patient.

21. The method of claim 20, further comprising adapting a sensitivity of the breath interval threshold or the tidal volume threshold based on one or more previously detected episodes of disordered breathing.

22. The method of claim 17, wherein classifying the respiration pattern as disordered breathing comprises classifying the respiration pattern as periodic breathing.

23. The method of claim 17, wherein classifying the respiration pattern as disordered breathing comprises classifying the respiration pattern as Cheyne-Stokes breathing.

24. A device for detecting sleep-disordered breathing of a patient, comprising:
a sensor system configured to detect a respiration pattern of one or more respiration cycles; and
a detector system coupled to the sensor system and configured to:
determine one or more breath intervals and one or more tidal volume measurements of the one or more respiration cycles;
identify an ongoing disordered breathing event as one or both of an apnea event and a hypopnea event based on comparison of the breath intervals to a breath interval threshold or the tidal volume measurements to a tidal volume threshold;
determine a duration of the ongoing disordered breathing event; and if the ongoing disordered breathing duration exceeds an event duration threshold, discriminating between apnea, hypopnea and mixed apnea and hypopnea using the one or more characteristics of the respiration pattern, wherein at least one of the sensor system and the detector system uses an implantable component.

25. The device of claim 24, wherein each of the sensor system and the detector system uses an implantable component.

26. The device of claim 24, wherein the sensor system is configured to detect the respiration patterns by measuring transthoracic impedance.

27. The device of claim 24, wherein the detector system is configured to establish one or both of the breath interval threshold or the tidal volume threshold for a particular patient.

28. The device of claim 27, wherein the detector system is configured to modify the breath interval threshold or the tidal volume threshold based on a condition of the patient.

29. The device of claim 24, wherein the detector system is configured to adapt a sensitivity of the breath interval threshold or the tidal volume threshold based on one or more previously detected episodes of sleep-disordered breathing.

30. The device of claim 24, wherein the detector system is configured to determine a non-breathing interval.

31. The device of claim 30, wherein the detector system is configured to compare the non-breathing interval to a predetermined sleep apnea interval and classify the respiration pattern as sleep apnea based on the comparison.

32. The device of claim 30, wherein the detector system is configured to compare the non-breathing interval to a predetermined severe sleep apnea interval and classify the respiration pattern as severe sleep apnea based on the comparison.

33. The device of claim 24, wherein the detector system is configured to compare the tidal volume of each respiration cycle to a tidal volume threshold, compare the duration of the respiration pattern to a predetermined duration threshold, and classify the respiration pattern as hypopnea based on the comparison.

34. The device of claim 24, wherein the detector system is configured to determine the breath interval threshold or the tidal volume threshold of the respiration pattern.

35. The device of claim 34, wherein the detector system is configured to compare the breath interval or the tidal volume measurement of the respiration pattern to the breath interval threshold or the tidal volume threshold and classify the respiration pattern as sleep-disordered breathing based on the comparison.

36. The device of claim 24, wherein the detector system is configured to compare the breathing interval of each respiration cycle to a predetermined duration threshold and classify the respiration pattern as apnea based on the comparison.

37. A device for detecting disordered breathing of a patient, comprising:
   a sensor system configured to detect a respiration pattern of one or more respiration cycles; and
   a detector system coupled to the sensor system and configured to:
      determine one or more breath intervals and one or more tidal volume measurements of the one or more respiration cycles;
      identify an ongoing disordered breathing event as one or both of an apnea event and a hypopnea event based on comparison of the breath intervals to a breath interval threshold or the tidal volume measurements to a tidal volume threshold;
      determine a duration of the ongoing disordered breathing event; and if the ongoing disordered breathing duration exceeds an event duration threshold, discriminating between apnea, hypopnea and mixed apnea and hypopnea using the one or more characteristics of the respiration pattern, wherein at least one of the sensor system and the detector system uses an implantable component.

38. The device of claim 37, wherein the sensor system is configured to detect the respiration patterns by measuring transthoracic impedance.

39. The device of claim 37, wherein the detector is configured to establish a disordered breathing index, compare the one or more characteristics to the sleep-disordered breathing index, and classify the respiration patterns as disordered breathing based on the comparison.

40. The device of claim 39, wherein the detector system is configured to modify the breath interval threshold or the tidal volume threshold based on a condition of the patient.

41. The device of claim 39, wherein the detector system is configured to adapt a sensitivity of the breath interval threshold or the tidal volume threshold based on one or more previously detected episodes of disordered breathing.

42. A disordered breathing detection system, comprising:
   means for detecting a respiration pattern of one or more respiration cycles;
   means for determining characteristics of the respiration pattern, comprising:
      means for determining one or more breath intervals and one or more tidal volume measurements of the one or more respiration cycles;
      means for identifying an ongoing disordered breathing event as one or both of an apnea event and a hypopnea event based on comparison of the breath intervals to a breath interval threshold or the tidal volume measurements to a tidal volume threshold; and
      means for determining a duration of the ongoing disordered breathing event; and
   means for discriminating between apnea, hypopnea or mixed apnea and hypopnea respiration patterns based on the one or more characteristics of the respiration pattern if the ongoing disordered breathing duration exceeds an event duration threshold, wherein at least one of the means for detecting, means for determining and means for discriminating uses an implantable component.

43. The system of claim 42, wherein the means for detecting the respiration pattern comprises means for detecting the respiration pattern while the patient is awake.

44. The system of claim 42, wherein the means for detecting the respiration pattern comprises means for detecting the respiration pattern while the patient is asleep.

* * * * *

UNITED STATES PATENT AND TRADEMARK OFFICE
CERTIFICATE OF CORRECTION

| | |
|---|---|
| PATENT NO. | : 7,252,640 B2 |
| APPLICATION NO. | : 10/309770 |
| DATED | : August 7, 2007 |
| INVENTOR(S) | : Ni et al. |

It is certified that error appears in the above-identified patent and that said Letters Patent is hereby corrected as shown below:

<u>In the References Cited: U.S. Patent Documents item 56</u>

On title page, line 7: "6,752,767 B1* 6/2004 Strobel et al." should read --6,752,767 B1 * 6/2004 Jensen et al--.

Signed and Sealed this

Fourth Day of March, 2008

JON W. DUDAS
*Director of the United States Patent and Trademark Office*